United States Patent
Park et al.

(10) Patent No.: US 10,329,312 B2
(45) Date of Patent: Jun. 25, 2019

(54) LANTHANUM COMPOUND, METHOD OF SYNTHESIZING LANTHANUM COMPOUND, LANTHANUM PRECURSOR COMPOSITION, METHOD OF FORMING THIN FILM, AND METHOD OF MANUFACTURING INTEGRATED CIRCUIT DEVICE

(71) Applicant: SAMSUNG ELECTRONICS CO., LTD., Suwon-si, Gyeonggi-do (KR)

(72) Inventors: Gyu-hee Park, Hwaseong-si (KR); Youn-soo Kim, Yongin-si (KR); Jae-soon Lim, Seoul (KR); Youn-joung Cho, Hwaseong-si (KR); Haruyoshi Sato, Tokyo (JP); Naoki Yamada, Tokyo (JP); Hiroyuki Uchiuzou, Tokyo (JP)

(73) Assignees: Samsung Electronics Co., Ltd., Suwon-Si, Gyeonggi-do (KR); Adeka Corporation, Tokyo (JP)

( * ) Notice: Subject to any disclaimer, the term of this patent is extended or adjusted under 35 U.S.C. 154(b) by 238 days.

(21) Appl. No.: 15/092,953

(22) Filed: Apr. 7, 2016

(65) Prior Publication Data
US 2017/0008914 A1 Jan. 12, 2017

(30) Foreign Application Priority Data
Jul. 7, 2015 (KR) .................. 10-2015-0096785

(51) Int. Cl.
C07F 7/10 (2006.01)
(52) U.S. Cl.
CPC ..................................... *C07F 7/10* (2013.01)
(58) Field of Classification Search
None
See application file for complete search history.

(56) References Cited

U.S. PATENT DOCUMENTS

| | | |
|---|---|---|
| 7,081,421 B2 | 7/2006 | Ahn et al. |
| 8,012,536 B2 | 9/2011 | Shenai-Khatkhate et al. |
| 8,071,452 B2 | 12/2011 | Raisanen |
| 8,206,784 B2 | 6/2012 | Xu et al. |
| 8,236,381 B2 | 8/2012 | Okubo |
| 8,283,201 B2 | 10/2012 | Pallem et al. |
| 8,617,305 B2 | 12/2013 | Lei et al. |
| 8,617,649 B2 | 12/2013 | Dussarrat et al. |
| 8,809,849 B2 | 8/2014 | Pallem et al. |
| 8,877,655 B2 | 11/2014 | Shero et al. |
| 2004/0164357 A1 | 8/2004 | Ahn et al. |
| 2006/0072281 A1 | 4/2006 | Nam et al. |
| 2007/0059447 A1 | 3/2007 | Kim et al. |
| 2009/0117274 A1 | 5/2009 | Ma et al. |
| 2010/0034719 A1 | 2/2010 | Dussarrat et al. |
| 2011/0184156 A1 | 7/2011 | Jones |
| 2011/0275166 A1 | 11/2011 | Shero et al. |

FOREIGN PATENT DOCUMENTS

| | | | | |
|---|---|---|---|---|
| JP | 200613267 | * | 1/2006 | ........... H01L 21/316 |
| KR | 10-0590051 B1 | | 6/2006 | |
| KR | 10-0684992 B1 | | 2/2007 | |
| WO | WO 2004/046417 A2 | | 6/2004 | |

OTHER PUBLICATIONS

JP-200613267 machine translation from Google patents (2006).*
Chiang, et al., "Effects of $La_2O_3$ Capping Prepared by Different ALD Lanthanum Precursors on Flatband Voltage Tuning and EOT Scaling in $TiN/HfO_2/SiO_2/Si$ MOS Structures" Journal of the Electrochemical Society, 158(4) H447-H451 (2011).

* cited by examiner

*Primary Examiner* — Clinton A Brooks
(74) *Attorney, Agent, or Firm* — Lee & Morse, P.C.

(57) ABSTRACT

A silicon-containing intermediate is synthesized by reacting a lanthanum tris[bis(trialkylsilyl)amide] complex with an alkylcyclopentadiene. A lanthanum compound is synthesized by reacting the silicon-containing intermediate with a dialkylamidine-based compound.

16 Claims, 34 Drawing Sheets

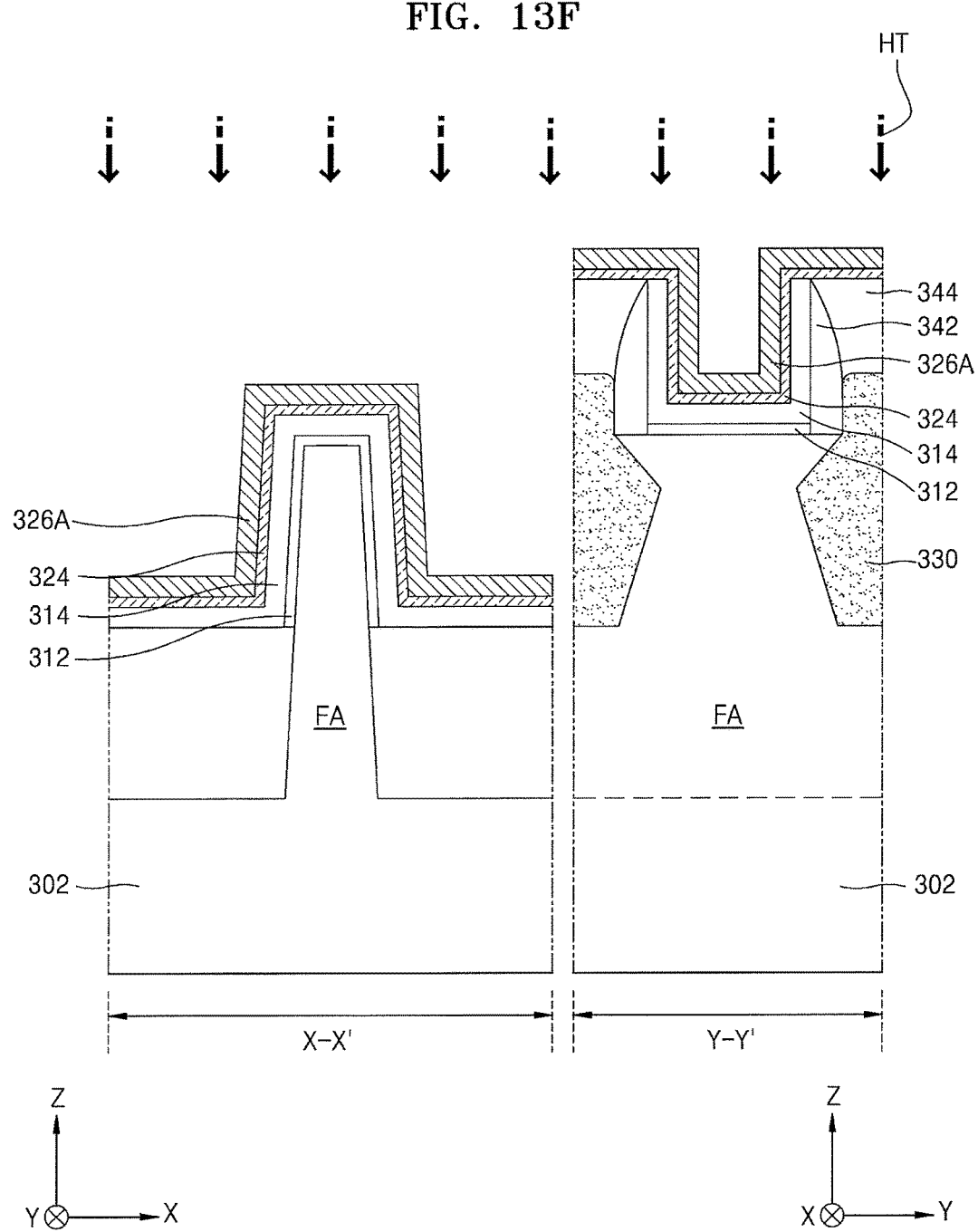

A – A'

B – B'

LANTHANUM COMPOUND, METHOD OF SYNTHESIZING LANTHANUM COMPOUND, LANTHANUM PRECURSOR COMPOSITION, METHOD OF FORMING THIN FILM, AND METHOD OF MANUFACTURING INTEGRATED CIRCUIT DEVICE

CROSS-REFERENCE TO RELATED APPLICATION

Korean Patent Application No. 10-2015-0096785, filed on Jul. 7, 2015, in the Korean Intellectual Property Office, and entitled: "Lanthanum Compound, Method of Synthesizing Lanthanum Compound, Lanthanum Precursor Composition, Method of Forming Thin Film, and Method of Manufacturing Integrated Circuit Device," is incorporated by reference herein in its entirety.

BACKGROUND

1. Field

Embodiments relate to a lanthanum compound, a method of synthesizing lanthanum compound, a lanthanum precursor composition, a method of forming thin film, and a method of manufacturing integrated circuit device.

2. Description of the Related Art

With the development of electronic technology, semiconductor devices have rapidly been downscaled, and patterns constituting electronic devices have been miniaturized. Also, a variety of research has been conducted on IC devices having high operating speed and high reliability.

SUMMARY

Embodiments are directed to a synthesis method, the method including synthesizing a silicon-containing intermediate of Chemical Formula 1 by reacting a lanthanum tris[bis(trialkylsilyl)amide] complex with an alkylcyclopentadiene, (1)

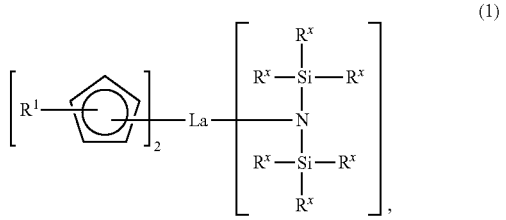

wherein $R^1$ may be a C1-C4 linear or branched alkyl group, and $R^x$ may independently be a C1-C2 alkyl group, and synthesizing a lanthanum compound of Chemical Formula 2 by reacting the silicon-containing intermediate of Chemical Formula 1 with a dialkylamidine-based compound, (2)

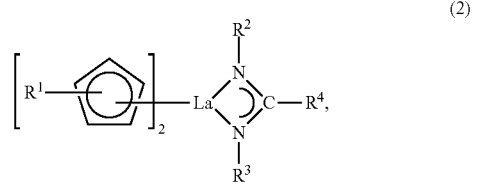

wherein $R^1$ may be a C1-C4 linear or branched alkyl group, each of $R^2$ and $R^3$ may be independently a C1-C4 linear or branched alkyl group, and $R^4$ may be hydrogen atom or a methyl group.

In the silicon-containing intermediate of Chemical Formula 1, $R^x$ may be a methyl group.

The lanthanum compound of Chemical Formula 2 may be a liquid at room temperature.

The dialkylamidine-based compound may be formed from diisopropyl acetamidine.

In the lanthanum compound of Chemical Formula 2, $R^1$ may be an ethyl group, each of $R^2$ and $R^3$ may be an isopropyl group, and $R^4$ may be a methyl group.

In the lanthanum compound of Chemical Formula 2, each of $R^1$, $R^2$, and $R^3$ may be an isopropyl group, and $R^4$ may be a methyl group.

In the lanthanum compound of Chemical Formula 2, $R^1$ may be an isopropyl group, each of $R^2$ and $R^3$ may be a t-butyl group, and $R^4$ may be a methyl group.

The method may further include, before the synthesizing of the silicon-containing intermediate, synthesizing the lanthanum tris[bis(trialkylsilyl)amide] complex by reacting a lanthanum halide with a bis(trialkylsilyl)amide alkali metal salt.

The lanthanum halide may be $LaCl_3$.

The bis(trialkylsilyl)amide alkali metal salt may include sodium (Na), lithium (Li), or potassium (K).

Embodiments are also directed to a lanthanum compound of Chemical Formula 2, which is synthesized by the method as described above.

The lanthanum compound may be a liquid at room temperature.

The lanthanum compound may be represented by the following chemical formula:

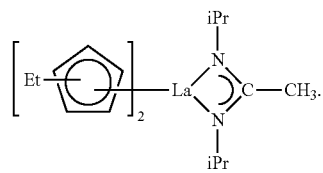

The lanthanum compound may be represented by the following chemical formula:

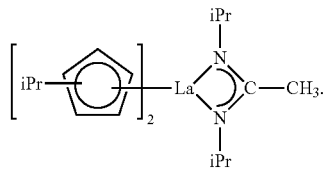

The lanthanum compound may be represented by the following chemical formula:

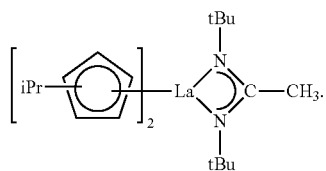

Embodiments are also directed to a lanthanum precursor composition, the composition including a lanthanum compound represented by the following chemical formula:

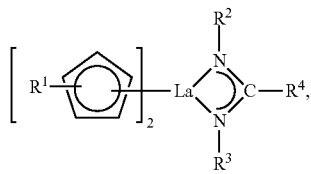

wherein $R^1$ may be a C1-C4 linear or branched alkyl group, each of $R^2$ and $R^3$ may independently be a C1-C4 linear or branched alkyl group, and $R^4$ may be hydrogen or a methyl group.

The composition may include one or more compounds represented by the following chemical formulas:

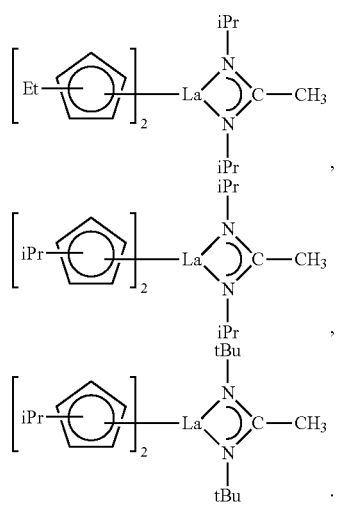

The composition may further include a silicon-containing compound.

The silicon-containing compound may include lanthanum (La).

The silicon-containing compound may be represented by the following Chemical Formula 1:

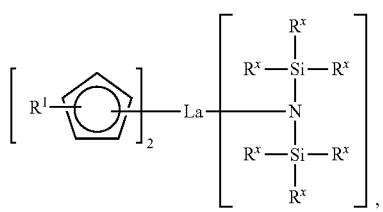

(1)

wherein $R^1$ may be a C1-C4 linear or branched alkyl group, and each $R^x$ may independently be a C1-C2 alkyl group.

$R^1$ may be an ethyl group and $R^x$ may be a methyl group.

The silicon-containing compound may be contained at a content of about 10 ppb to about 100 ppb, based on a total weight of the composition.

Embodiments are also directed to a method of forming a thin film, the method including forming a lanthanum-containing film on a substrate by using a lanthanum compound that is a liquid at room temperature, the lanthanum compound being represented by the following Chemical Formula 2:

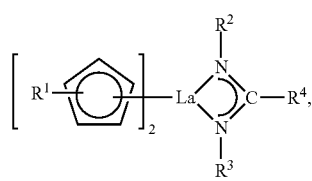

(2)

wherein $R^1$ may be a C1-C4 linear or branched alkyl group, each of $R^2$ and $R^3$ may independently be a C1-C4 linear or branched alkyl group, and $R^4$ may be hydrogen or a methyl group.

The lanthanum compound may include one or more compounds represented by the following chemical formulas:

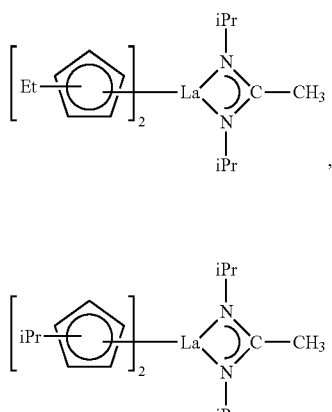

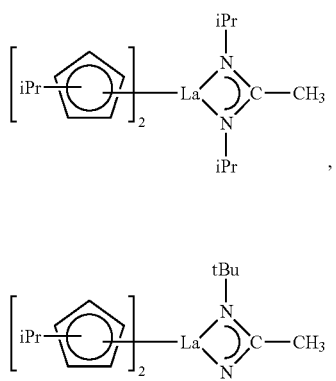

The forming of the lanthanum-containing film may be performed at a temperature of about 150° C. to about 500° C. under a pressure that may be from atmospheric pressure to a pressure of about 10 Pa.

The forming of the lanthanum-containing film may include forming a vaporized source gas containing the lanthanum compound, forming a lanthanum source adsorbed layer on the substrate by providing the vaporized source gas onto the substrate, and providing a reactive gas onto the lanthanum source adsorbed layer.

The vaporized source gas may contain only the lanthanum compound.

The vaporized source gas may contain the lanthanum compound and a silicon-containing compound represented by the following Chemical Formula 1:

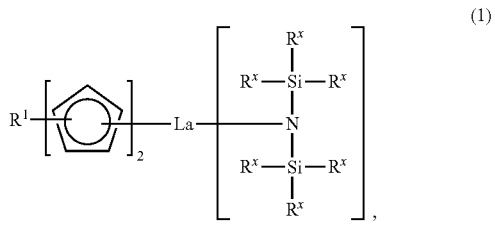

(1)

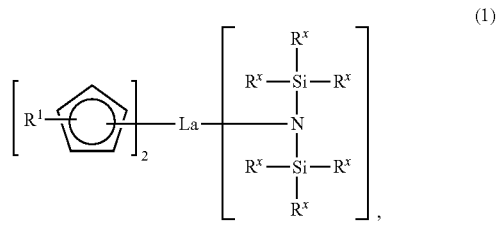

(1)

wherein $R^1$ may be a C1-C4 linear or branched alkyl group, and each $R^x$ may independently be a C1-C2 alkyl group.

The reactive gas may include $O_2$, $O_3$, plasma $O_2$, $H_2O$, $NO_2$, NO, $CO_2$, $H_2O_2$, or a combination thereof.

Embodiments are also directed to a method of manufacturing an integrated circuit (IC) device, the method including forming a lower structure on a substrate, and forming a lanthanum-containing film on the lower structure by using a lanthanum compound which is a liquid at room temperature and represented by the following Chemical Formula 2:

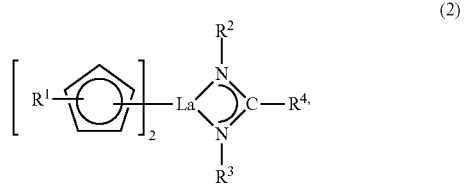

(2)

wherein $R^1$ may be a C1-C4 linear or branched alkyl group, each of $R^2$ and $R^3$ may independently be a C1-C4 linear or branched alkyl group, and $R^4$ may be hydrogen or a methyl group.

The method may further include diffusing lanthanum atoms from the lanthanum-containing film into a partial region of the lower structure by heat-treating a resultant structure that includes the lanthanum-containing film.

The forming of the lower structure may include forming a fin-type active region by etching a portion of the substrate, the fin-type active region protruding upward from the substrate, forming an interface layer on a surface of the fin-type active region, and forming a high-k dielectric film on the interface layer, and the lanthanum-containing film may be formed on the high-k dielectric film.

The method may further include diffusing lanthanum atoms into an interface between the interface layer and the high-k dielectric film by heat-treating a resultant structure including the lanthanum-containing film.

The forming of the lower structure may include forming a word line trench by etching a portion of the substrate, and the forming of the lanthanum-containing film may include forming a gate dielectric film including a $La_2O_3$ film within the word line trench.

The forming of the lower structure may include forming a structure including a buried contact hole exposing a portion of an active region of the substrate, and the forming of the lanthanum-containing film may include forming a $La_2O_3$ film that is in contact with the portion of the active region exposed by the buried contact hole.

Embodiments are also directed to a compound represented by the following Chemical Formula 1:

wherein $R^1$ may be a C1-C4 linear or branched alkyl group, and each $R^x$ may independently be a C1-C2 alkyl group.

The compound may be substantially pure.

Embodiments are also directed to a method of forming the compound of Chemical Formula 1, the method including reacting a lanthanum tris(alkylsilylamide) complex with an alkylcyclopentadiene, wherein, in the lanthanum tris(alkylsilylamide) complex, the alkyl groups may each independently be a C1-C2 alkyl group, and, in the alkylcyclopentadiene, the alkyl group may be a C1-C4 linear or branched alkyl group.

The method may further include purifying the resultant of the reaction of the lanthanum tris(alkylsilylamide) complex with the alkylcyclopentadiene.

The purifying may include sublimation of the compound represented by Chemical Formula 1.

Embodiments are also directed to a method of manufacturing an integrated circuit (IC) device using the compound of Chemical Formula 1, the method including forming a lower structure on a substrate, and forming a lanthanum-containing film on the lower structure, the lanthanum-containing film being produced by deposition of lanthanum-containing species from a composition that includes the compound represented by Chemical Formula 1 and a compound represented by the following Chemical Formula 2:

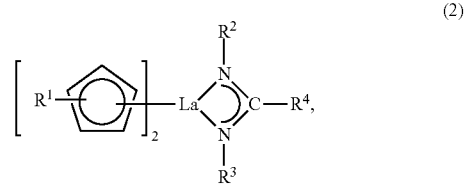

(2)

wherein, in Chemical Formula 2, $R^1$ may be a C1-C4 linear or branched alkyl group, each of $R^2$ and $R^3$ may independently be a C1-C4 linear or branched alkyl group, and $R^4$ may be hydrogen or a methyl group.

BRIEF DESCRIPTION OF THE DRAWINGS

Features will become apparent to those of skill in the art by describing in detail example embodiments with reference to the attached drawings in which:

FIGS. 13A to 13G illustrate cross-sectional views of process operations of a method of manufacturing an IC device according to an example embodiment;

FIGS. 17A to 17C illustrate cross-sectional views of examples of an IC device including a lanthanum-containing film formed by using a lanthanum compound according to an example embodiment, wherein FIG. 17A is a cross-sectional view of some elements corresponding to a line A-A' of FIG. 16, FIG. 17B is a cross-sectional view of some elements corresponding to a line B-B' of FIG. 16, and FIG. 17C is a cross-sectional view of some elements corresponding to a line C-C' of FIG. 16;

DETAILED DESCRIPTION

Figure 1:
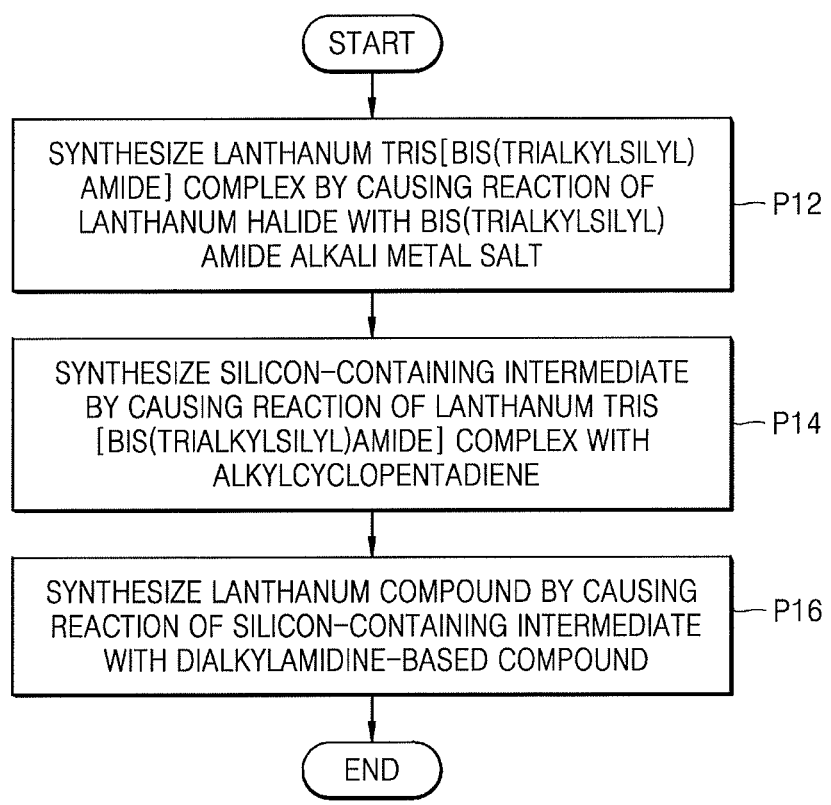
FIG. 1 illustrates a flowchart of a method of synthesizing a lanthanum compound according to an example embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art.

In the drawing figures, the dimensions of layers and regions may be exaggerated for clarity of illustration. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

It will be understood that, although the terms first, second, etc. may be used herein to describe various elements, components, regions, layers and/or sections, these elements, components, regions, layers and/or sections should not be limited by these terms. Thus, a first element, component, region, layer or section discussed below could be termed a second element, component, region, layer or section without departing from the teachings of the inventive concept.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and this specification and will not be interpreted in an idealized or overly formal sense unless explicitly so defined herein.

When some embodiments may be embodied otherwise, respective process steps described herein may be performed otherwise. For example, two process steps described in a sequential order may be performed substantially the same time or in reverse order.

Variations from the shapes of the illustrations as a result, for example, of manufacturing techniques and/or tolerances, are to be expected. Thus, embodiments of the inventive concept should not be construed as limited to the particular shapes of regions illustrated herein but are to include deviations in shapes that result, for example, from manufacturing. When a term "substrate" is used herein, it may refer to either the substrate itself or both the substrate and a stack structure including a predetermined layer or film formed on the substrate. Also, when an expression "surface of the substrate" is used herein, it may refer to either as an exposed surface of the substrate itself or an outer surface of a predetermined layer or film formed on the substrate. As used herein, a term "Me" refers to a methyl group, a term "Et" refers to an ethyl group, a term "iPr" refers to an isopropyl group, and a term "tBu" refers to a tertiary butyl group.

FIG. 1 is a flowchart of a method of synthesizing a lanthanum compound according to an example embodiment.

Referring to FIG. 1 and Reaction Equation 1 (below), in a process P12, a lanthanum halide may be reacted with a bis(trialkylsilyl)amide alkali metal salt to synthesize a lanthanum tris[bis(trialkylsilyl)amide] complex A-1.

In some embodiments, the lanthanum halide may be $LaCl_3$.

Reaction Equation 1 shows an example of the process P12 of forming the lanthanum tris[bis(trialkylsilyl)amide] complex A-1 (tris[N,N-bis(trialkylsilyl)amide]lanthanum(III)).

[Reaction Equation 1]

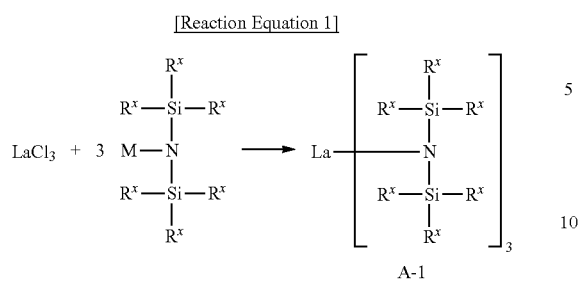

In Reaction Equation 1, M is an alkali metal, and each $R^x$ is independently a C1-C2 alkyl group.

In some embodiments, M may be sodium (Na), lithium (Li), or potassium (K).

As shown in Reaction Equation 1, anhydrous lanthanum chloride ($LaCl_3$) as a lanthanum halide may be reacted with the bis(trialkylsilyl)amide alkali metal salt to synthesize the lanthanum tris[bis(trialkylsilyl)amide] complex A-1, which serves as a reaction intermediate. The lanthanum tris[bis(trialkylsilyl)amide] complex A-1 may be re-crystallized for use as the reaction intermediate.

In a process P14 of FIG. 1, the lanthanum tris[bis(trialkylsilyl)amide] complex A-1 obtained in the process P12 may be reacted with an alkylcyclopentadiene to synthesize a silicon-containing intermediate represented by Chemical Formula 1 (also referred to herein using the shorthand CF-1).

[Chemical Formula 1]

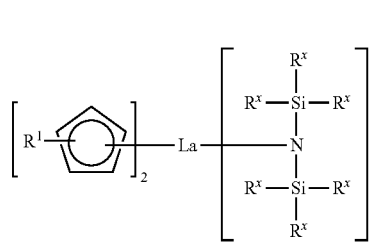

In Chemical Formula 1, $R^1$ may be a C1-C4 linear or branched alkyl group, and $R^x$ is the same as defined above.

Reaction Equation 2 shows an example of a process of forming the silicon-containing intermediate CF-1 using the process P14.

[Reaction Equation 2]

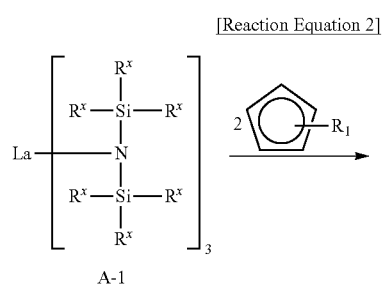

-continued

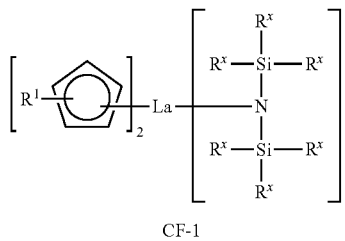

CF-1

In Reaction Equation 2, $R^1$ and $R^x$ are the same as defined above.

In some embodiments, in Reaction Equation 2, $R^1$ may be an ethyl group, and $R^x$ may be, e.g., a methyl group.

As shown in Reaction Equation 2, the lanthanum tris[bis(trialkylsilyl)amide] complex A-1 obtained in Reaction Equation 1 may be reacted with cyclopentadienyl derivative having a desired structure to synthesize the silicon-containing intermediate CF-1. The silicon-containing intermediate CF-1 may be purified by using, e.g., a sublimation process.

In a process P16 of FIG. 1, the silicon-containing intermediate CF-1, which is obtained in the process P14, may be reacted with a dialkylamidine-based compound to synthesize a lanthanum compound represented by Chemical Formula 2 (also referred to herein using the shorthand CF-2).

[Chemical Formula 2]

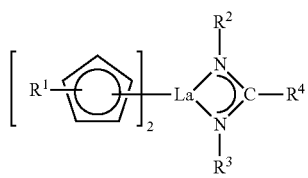

In Chemical Formula 2, $R^1$ is the same as defined above, each of $R^2$ and $R^3$ may independently be a C1-C4 linear or branched alkyl group, and $R^4$ may be hydrogen or a methyl group.

Reaction Equation 3 shows an example of a process of preparing the lanthanum compound CF-2 using the process P16.

[Reaction Equation 3]

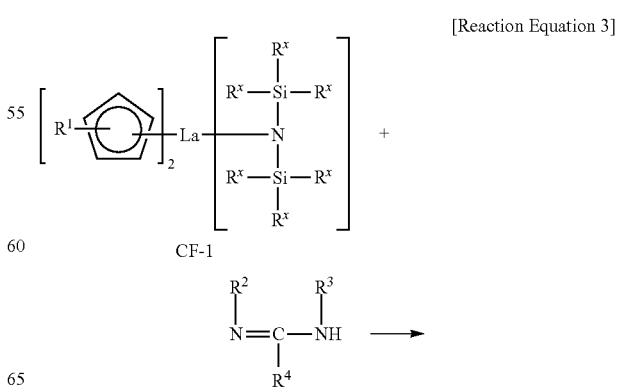

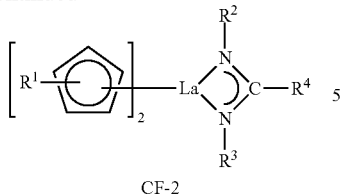

CF-2

In Reaction Equation 3, $R^1$, $R^2$, $R^3$, and $R^4$ are the same as defined above.

In some embodiments, in Reaction Equation 3, $R^1$ may be an ethyl group, and $R^x$ may be a methyl group.

In Reaction Equation 3, each of $R^2$ and $R^3$ may be, e.g., an isopropyl group, and the dialkylamidine-based compound used in the process P16 of FIG. 1 may be formed from diisopropyl acetamidine.

As shown in Reaction Equation 3, the silicon-containing intermediate CF-1 may be reacted with dialkylamidine, thereby preparing the lanthanum compound CF-2 according to an example embodiment. The lanthanum compound CF-2 may be distilled in order to purify it.

In some embodiments, in the lanthanum compound CF-2, $R^1$ may be an ethyl group, each of $R^2$ and $R^3$ may be an isopropyl group, and $R^4$ may be a methyl group. In this case, the lanthanum compound CF-2 may be represented by Chemical Formula 3.

[Chemical Formula 3]

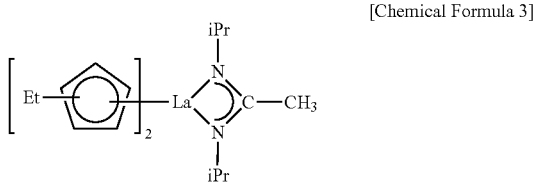

In some other embodiments, in the lanthanum compound CF-2, each of $R^1$, $R^2$, and $R^3$ may be an isopropyl group, and $R^4$ may be a methyl group. In this case, the lanthanum compound CF-2 may be represented by Chemical Formula 4.

[Chemical Formula 4]

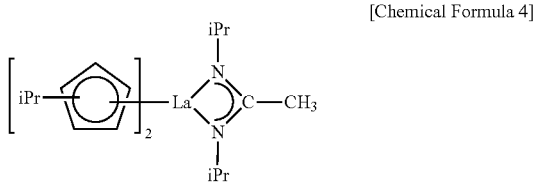

In some other embodiments, in the lanthanum compound CF-2, $R^1$ may be an isopropyl group, each of $R^2$ and $R^3$ may be a t-butyl group, and $R^4$ may be a methyl group. In this case, the lanthanum compound CF-2 may be represented by Chemical Formula 5.

[Chemical Formula 5]

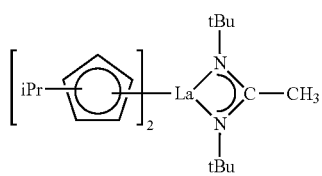

A lanthanum compound according to example embodiments may include the lanthanum compound CF-2, which may be obtained using the method of preparing the lanthanum compound as described with reference to FIG. 1. The lanthanum compound according to the example embodiments may be a liquid at room temperature. The lanthanum compound according to the example embodiments may be appropriately used as a lanthanum precursor when a thin film is formed by using a deposition process (e.g., an atomic layer deposition (ALD) process or a chemical vapor deposition (CVD) process) including a vaporization process. Also, since the lanthanum compound according to the example embodiments is highly reactive to a reactive gas (e.g., $O_3$), the lanthanum compound may be appropriately used as a lanthanum precursor used in, for example, an ALD process.

The lanthanum compound CF-2 may be used in a thin film forming process used for the manufacture of an IC device.

The lanthanum compound CF-2 may be used as a material of a lanthanum precursor composition for forming a lanthanum-containing film (e.g., a lanthanum oxide film) that may constitute an IC device or be used for a process of manufacturing the IC device.

In some embodiments, a lanthanum precursor composition may include only the lanthanum compound CF-2 obtained by using the method described above with reference to FIG. 1. In this case, the lanthanum precursor composition may include at least one of lanthanum compounds represented by Chemical Formula 3, Chemical Formula 4, and Chemical Formula 5.

In some other embodiments, the lanthanum precursor composition may include the lanthanum compound CF-2 obtained by using the method described above with reference to FIG. 1 and a silicon-containing compound. The silicon-containing compound included in the lanthanum precursor composition according to an example embodiment may include the silicon-containing intermediate compound CF-1, which is a reactant of Reaction Equation 3. For example, in the silicon-containing compound included in the lanthanum precursor composition according to the example embodiment, in the silicon-containing intermediate CF-1, $R^1$ may be an ethyl group, and $R^x$ may be a methyl group. In some embodiments, the silicon-containing compound included in the lanthanum precursor composition according to the example embodiment may be used as a reactant in a process of synthesizing the lanthanum compound CF-2. After the lanthanum compound CF-2 is formed, a reactant including the silicon-containing compound may be left in a very small amount in a final product so that the lanthanum precursor composition according to the example embodiment may include the silicon-containing compound.

For example, in the lanthanum precursor composition, the silicon-containing compound may be contained at a content of about 10 parts per billion (ppb) to about 100 ppb, based on the total weight of the lanthanum precursor composition.

Figure 2A:
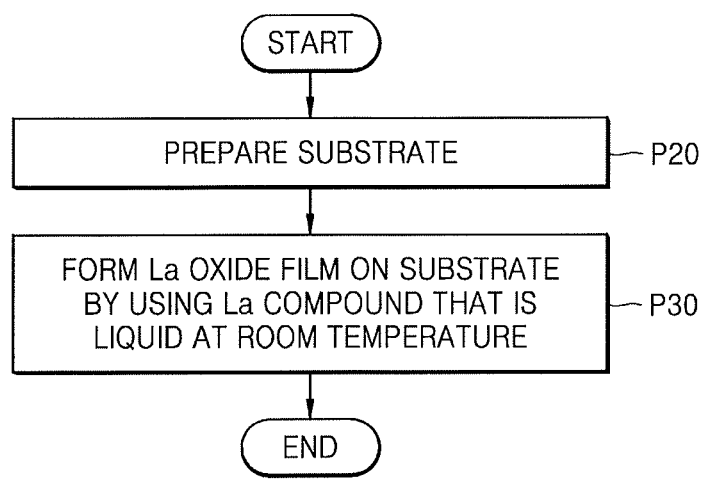
FIG. 2A illustrates a flowchart of a method of forming a thin film according to example embodiments.

FIG. 2A is a flowchart of a method of forming a thin film according to example embodiments.

Referring to FIG. 2A, a substrate may be prepared in a process P20.

The substrate may have the same configuration as a substrate 302 that will be described later with reference to FIGS. 12A to 12C.

In a process P30 of FIG. 2A, a lanthanum oxide film may be formed on the substrate by using a lanthanum compound that is a liquid at room temperature.

The lanthanum compound that is the liquid at room temperature may include a lanthanum compound having a structure of Chemical Formula 2. For example, the lanthanum compound that is the liquid at room temperature may include at least one of lanthanum compounds represented by Chemical Formula 3, Chemical Formula 4, and Chemical Formula 5.

In some embodiments, to form the lanthanum oxide film on the substrate using the process P30, a lanthanum precursor composition including only the lanthanum compound CF-2 that is obtained by using the method described with reference to FIG. 1 may be used.

In some other embodiments, to form the lanthanum oxide film on the substrate using the process P30, a lanthanum precursor composition including the lanthanum compound CF-2 that is obtained by using the method described with reference to FIG. 1 and a silicon-containing compound may be used. The silicon-containing compound may include the silicon-containing intermediate CF-1, which is the reactant of Reaction Equation 3. The silicon-containing compound may be contained at a content of, for example, about 10 ppb to about 100 ppb, based on the total weight of the lanthanum precursor composition.

Figure 2B:
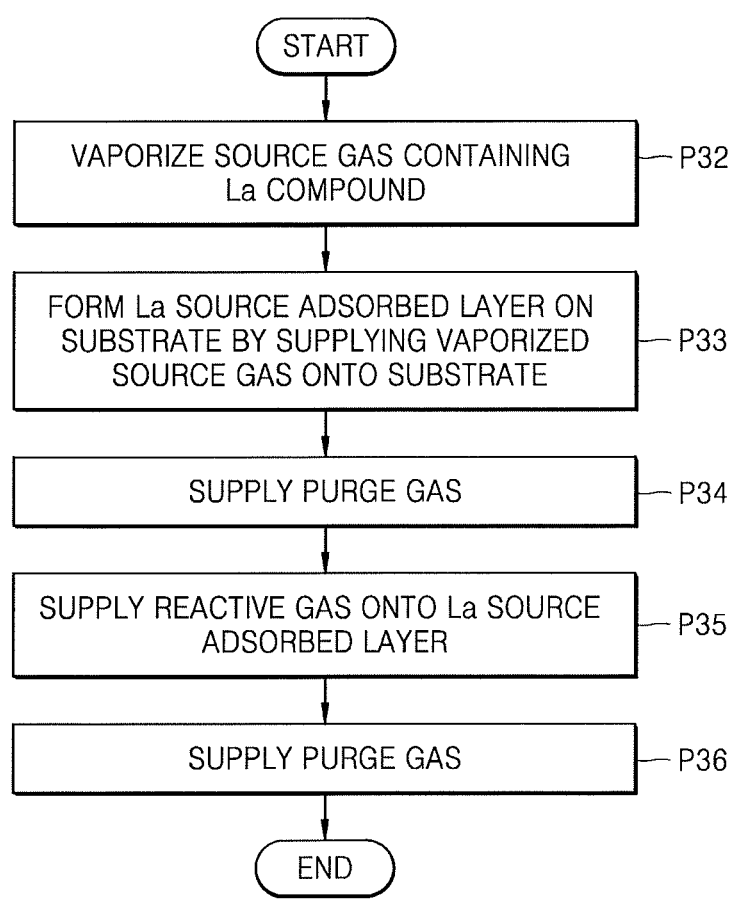
FIG. 2B illustrates a flowchart of a method of forming a lanthanum oxide film by using a method of forming a thin film according to example embodiments.

FIG. 2B is a flowchart of an example of a detailed method of forming a lanthanum oxide film using the process P30 of FIG. 2A.

Referring to FIG. 2B, in a process P32, a source gas containing a lanthanum compound may be vaporized. The lanthanum compound may include a lanthanum compound having a structure of Chemical Formula 2.

In some embodiments, the source gas may include only the lanthanum compound having the structure of Chemical Formula 2.

In some other embodiments, the source gas may include the lanthanum compound having the structure of Chemical Formula 2 and a silicon-containing compound. The silicon-containing compound may include the silicon-containing intermediate (A-2) of Chemical Formula 1, which is a reactant of Reaction Equation 3. For example, the silicon-containing compound contained in a lanthanum precursor composition according to an example embodiment may include the silicon-containing intermediate CF-1 in which $R^1$ is an ethyl group and $R^x$ is a methyl group.

In a process P33, the source gas that is vaporized using the process P32 may be supplied onto the substrate to form a lanthanum source adsorbed layer on the substrate.

By the vaporized source gas onto the substrate, an adsorbed layer including a chemisorbed layer and a physisorbed layer of the vaporized source gas may be formed on the substrate.

In a process P34, a purge gas may be supplied onto the substrate to eliminate unnecessary by-products from the substrate.

For example, an inert gas (e.g., argon (Ar) gas, helium (He) gas, or neon (Ne) gas) or nitrogen ($N_2$) gas may be used as the purge gas.

In some embodiments, a process of heating the substrate on which the lanthanum source adsorbed layer is formed or a process of heat-treating a reaction chamber in which the substrate is contained may be further performed. The heat treatment may be performed at room temperature to a temperature of about 400° C., for example, a temperature of about 150° C. to about 400° C.

In a process P35, a reactive gas may be supplied onto the lanthanum source adsorbed layer formed on the substrate.

The reactive gas may include $O_2$, $O_3$, plasma $O_2$, $H_2O$, $NO_2$, NO, $CO_2$, $H_2O_2$, or a combination thereof.

In a process P36, a purge gas may be supplied onto the substrate to eliminate unnecessary by-products from the substrate.

For example, an inert gas (e.g., Ar gas, He gas, and Ne gas) or $N_2$ gas may be used as the purge gas.

The method of forming the lanthanum oxide film described with reference to FIG. 2B is only an example and may be variously changed within the scope of the inventive concept.

For example, to form the lanthanum oxide film on the substrate, the lanthanum compound having the structure of Chemical Formula 2 may be simultaneously or sequentially supplied onto the substrate along with at least one of another precursor, a reactive gas, a carrier gas, and a purge gas. The another precursor, the reactive gas, the carrier gas, and the purge gas, which may be supplied onto the substrate along with the lanthanum compound having the structure of Chemical Formula 2, will be described in further detail later.

The lanthanum compound according to the example embodiment may be used in a thin-film forming process required to manufacture an IC device. For example, the lanthanum compound according to the example embodiment may be used as a lanthanum precursor used for an ALD process or a CVD process.

FIGS. 3 to 6 are schematic diagrams of configurations of deposition systems 200A, 200B, 200C, and 200D that may be used in a process of forming a thin film according to example embodiments.

Each of the deposition systems 200A, 200B, 200C, and 200D shown in FIGS. 3 to 6 may include a fluid transmission unit 210, a thin-film formation unit 250 configured to perform a deposition process of forming a thin film on a substrate W using a process gas supplied from a source container 212 included in the fluid transmission unit 210, and an exhaust system 270 configured to exhaust gases or by-products, which may remain after a reaction occurs in the thin-film formation unit 250.

The thin-film formation unit 250 may include a reaction chamber 254 including a susceptor 252 configured to support the substrate W. A shower head 256 may be installed at a top end unit of the inside of the reaction chamber 254. The shower head 256 may be configured to supply gas supplied from the fluid transmission unit 210 onto the substrate W.

The fluid transmission unit 210 may include an inlet line 222 configured to supply a carrier gas from the outside to the source container 212 and an outlet line 224 configured to supply a source compound contained in the source container 212 to the thin-film formation unit 250. A valve V1 and a mass flow controller (MFC) M1 may be installed at the inlet line 222, and a valve V2 and an MFC M2 may be installed at the outlet line 224. The inlet line 222 and the outlet line 224 may be connected to each other through a bypass line 226. A valve V3 may be installed at the bypass line 226. The valve V3 may operate due to a pneumatic pressure by using an electric motor or another remote control unit.

The source compound supplied from the source container 212 may be supplied into the reaction chamber 254 through the inlet line 266 of the thin-film formation unit 250, which is connected to the outlet line 224 of the fluid transmission unit 210. When necessary, the source compound supplied from the source container 212 may be supplied into the reaction chamber 254 together with a carrier gas supplied through an inlet line 268. A valve V4 and an MFC M3 may be installed at the inlet line 268 through which the carrier is supplied.

The thin-film formation unit 250 may include an inlet line 262 configured to supply a purge gas into the reaction chamber 254 and an inlet line 264 configured to supply a reactive gas. A valve V5 and an MFC M4 may be installed at the inlet line 262, and a valve V6 and an MFC M5 may be installed at the inlet line 264.

The process gas used in the reaction chamber 254 and reaction by-products to be discarded may be exhausted to the outside through an exhaust system 270. The exhaust system 270 may include an exhaust line 272 connected to the reaction chamber 254 and a vacuum pump 274 installed at the exhaust line 272. The vacuum pump 274 may serve to eliminate the process gas and the reaction by-products, which are exhausted from the reaction chamber 254.

A trap 276 may be installed in the exhaust line 272 at an upstream side of the vacuum pump 274. The trap 276 may trap, for example, reaction by-products, which are generated by unreacted process gases in the reaction chamber 254, and prevent the reaction by-products from flowing into the vacuum pump 274 disposed at a downstream side.

In a method of forming a thin film according to an example embodiment, the lanthanum compound having a structure of Chemical Formula 2, according to an example embodiment, may be used as a source compound. In particular, the lanthanum compound according to the example embodiment may be in a liquid state at room temperature and highly reactive with other process gases, for example, a reactive gas (e.g., a reducing gas). Accordingly, the trap 276 installed at the exhaust line 272 may function to trap attachments (e.g., reaction by-products), which may occur due to a reaction between the process gases, and prevent the attachments from flowing to a downstream side of the trap 276. The trap 276 may be configured to be cooled by a cooler or a water cooling device.

In addition, a bypass line 278 and an automatic pressure controller (APC) 280 may be installed in the exhaust line 272 at an upstream side of the trap 276. Valves V7 and V8 may be respectively installed in the bypass line 278 and a portion of the exhaust line 272, which may extend parallel to the bypass line 278.

Figure 3:
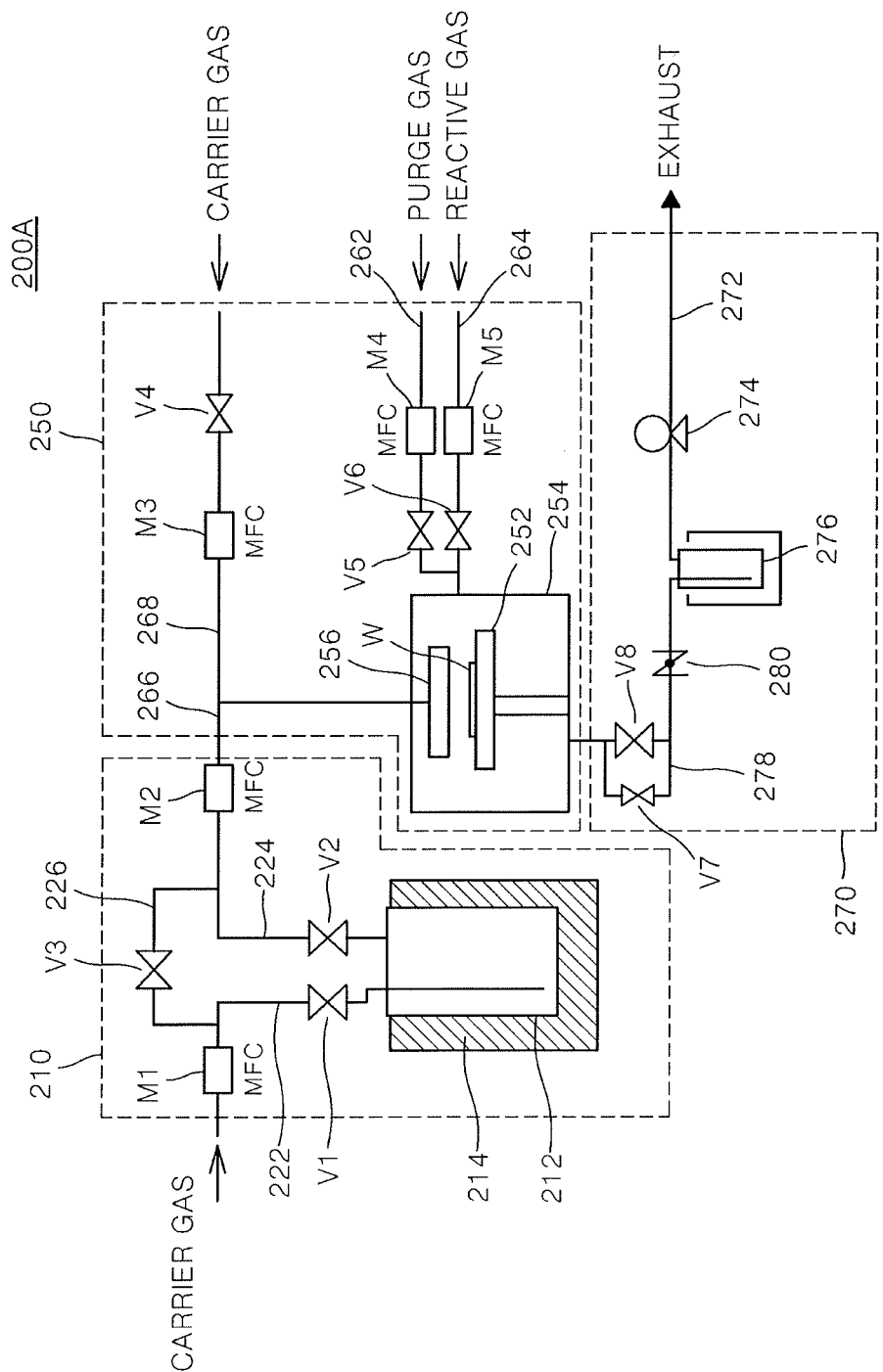
FIGS. 3 to 6 illustrate schematic diagrams of examples of a configuration of a deposition system that may be used in a process of forming a thin film according to an example embodiment.
Figure 5:
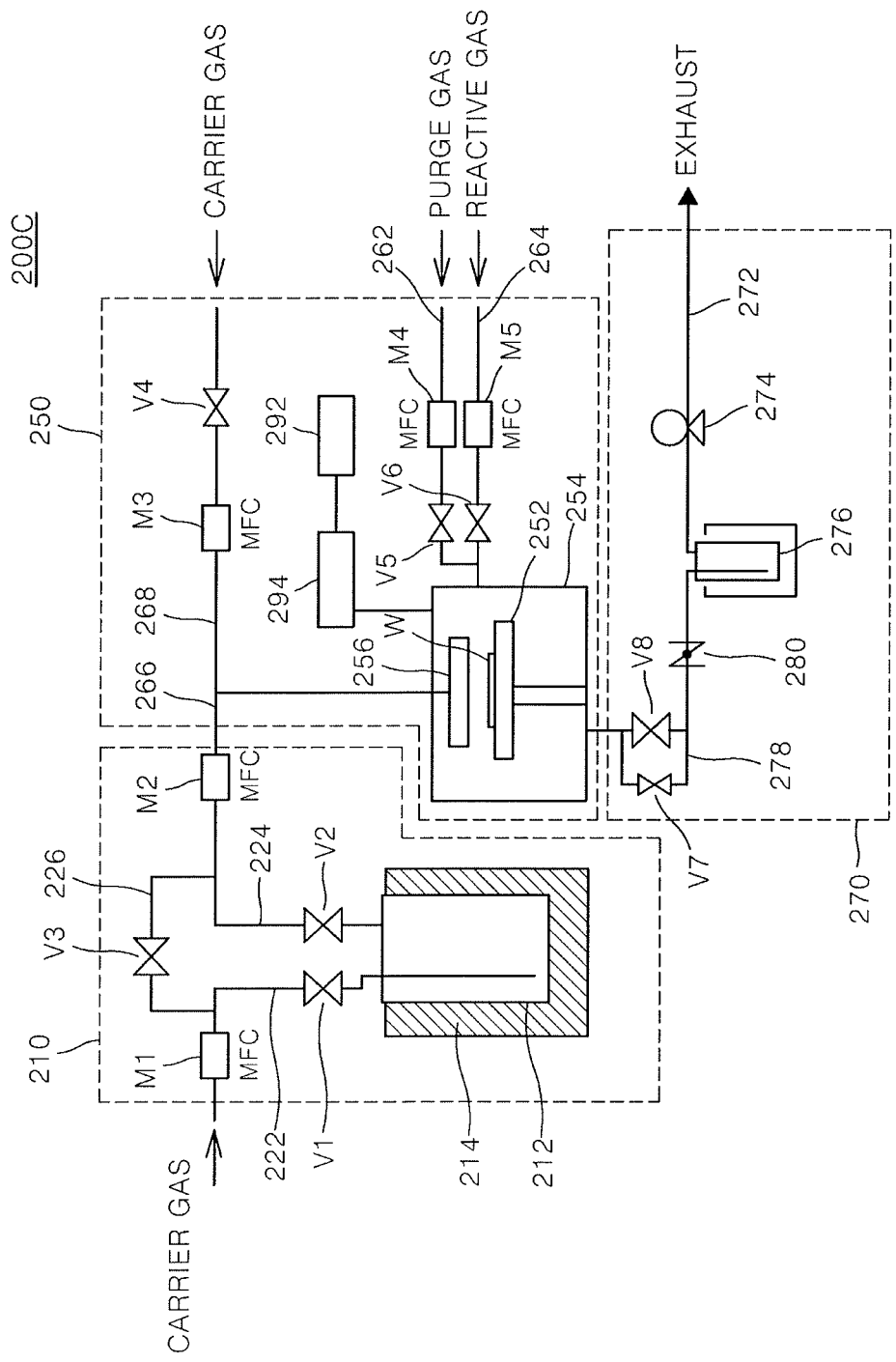

As in the deposition systems 200A and 200C shown in FIGS. 3 and 5, a heater 214 may be installed in the source container 212. A source compound contained in the source container 212 may be maintained at a relatively high temperature by the heater 214.

Figure 4:
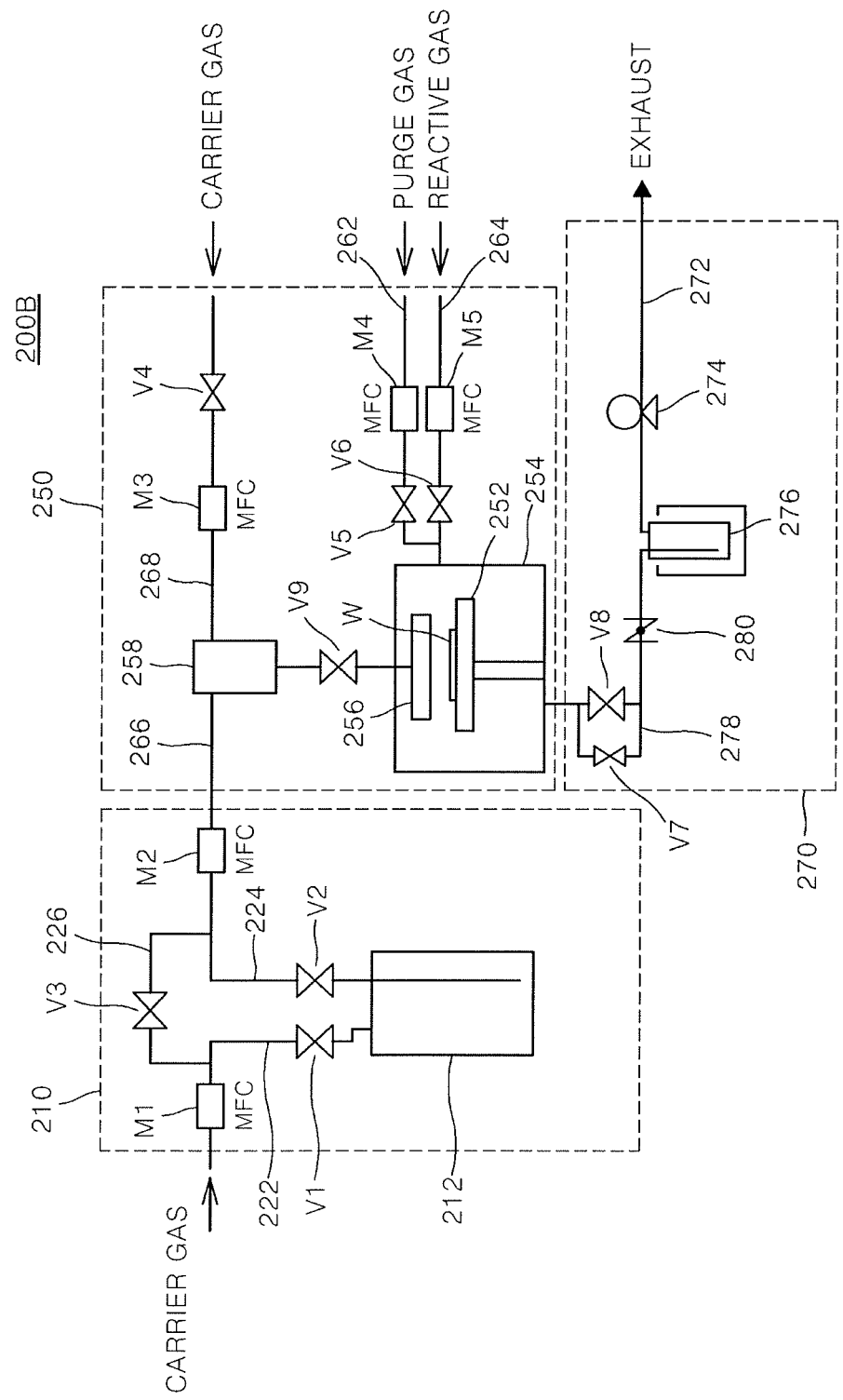
Figure 6:
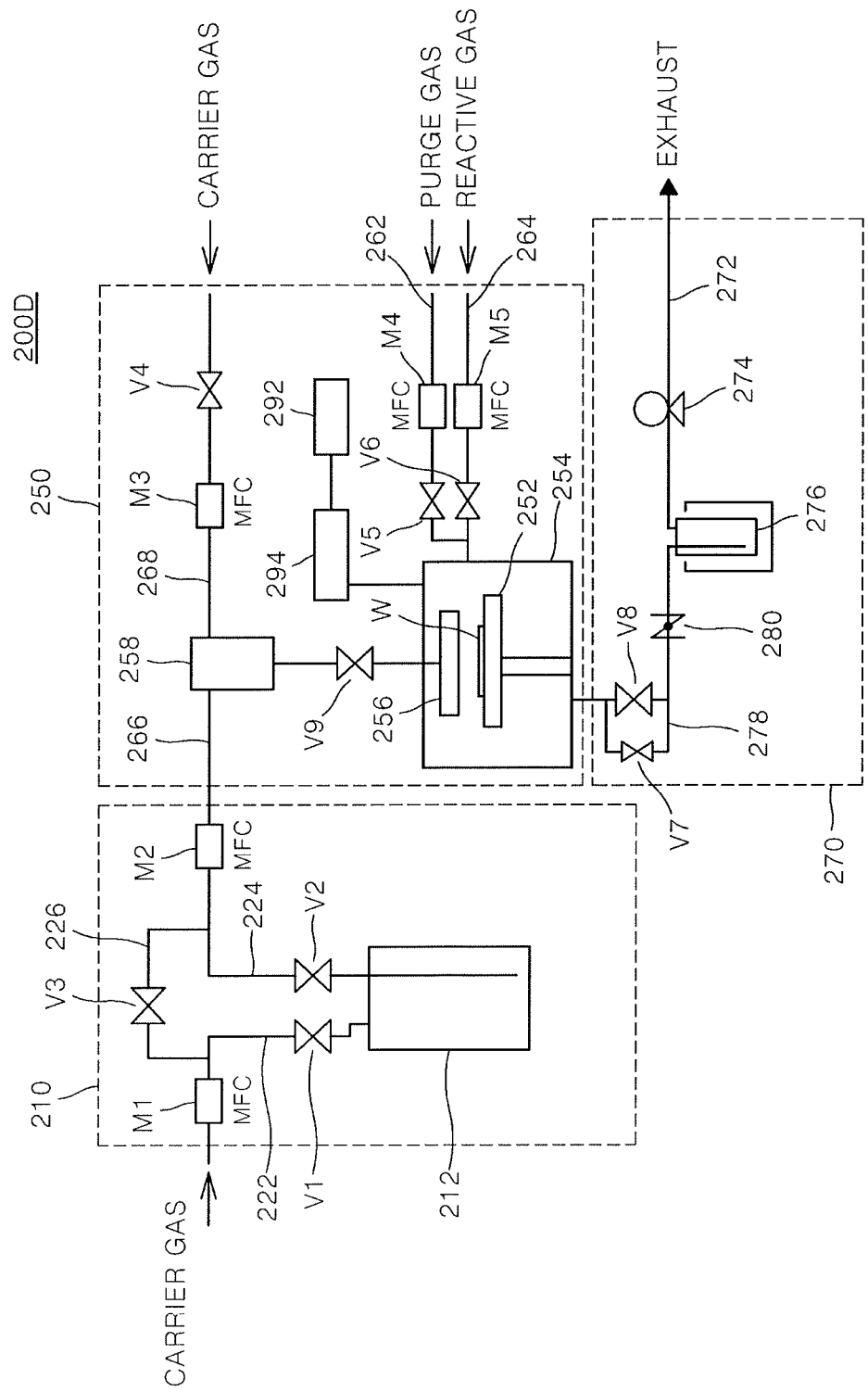

As in the deposition systems 200B and 200D shown in FIGS. 4 and 6, a vaporizer 258 may be installed at the inlet line 266 of the thin-film formation unit 250. The vaporizer 258 may vaporize a fluid supplied in a liquid state from the fluid transmission unit 210 and supply the vaporized source compound into the reaction chamber 254. The source compound vaporized by the vaporizer 258 may be supplied into the reaction chamber 254 together with a carrier gas supplied through the inlet line 268. The supplying of the source compound into the reaction chamber 254 through the vaporizer 258 may be controlled by a valve V9.

Furthermore, as in the deposition systems 200C and 200D shown in FIGS. 5 and 6, to generate plasma in the reaction chamber 254, the thin-film formation unit 250 may include a radio-frequency (RF) power source 292 and an RF matching system 294, which are connected to the reaction chamber 254.

FIGS. 3 to 6 illustrate the deposition systems 200A, 200B, 200C, and 200D in which one source container 212 is connected to the reaction chamber 254, but a plurality of source containers 212 may be provided in the fluid transmission unit 210, and each of the plurality of source containers 212 may be connected to the reaction chamber 254. The number of source containers 212 connected to the reaction chamber 254 may be varied.

In the process P32 of FIG. 2B, the source gas containing the lanthanum compound may be vaporized by using the vaporizer 258 of any one of the deposition systems 200B and 200D shown in FIGS. 4 and 6.

Furthermore, in the method of forming the thin film according to the example embodiment, any one of the deposition systems 200A, 200B, 200C, and 200D shown in FIGS. 3 to 6 may be used to form the lanthanum-containing film on the substrate W.

To form the lanthanum-containing film on the substrate W by using the processes described with reference to FIGS. 1, 2A, and 2B, the lanthanum compound having the structure of Chemical Formula 2, according to the example embodiment, may be transported by using various methods and supplied into a reaction chamber of a thin-film forming system, for example, the reaction chamber 254 of each of the deposition systems 200A, 200B, 200C, and 200D shown in FIGS. 3 to 6.

In some embodiments, to form a thin film via a CVD process by using the lanthanum compound having the structure of Chemical Formula 2, according to the example embodiment, a gas transporting method may be used. The gas transporting method may include vaporizing the lanthanum compound in the source container 212 by applying heat and/or reducing a pressure, and supplying the vaporized lanthanum compound together with a carrier gas (e.g., Ar, $N_2$, and He) into the reaction chamber 254 as needed. When the gas transporting method is used, the lanthanum compound according to the example embodiment itself may be used as a source compound for forming a thin film in the CVD process.

In some other embodiments, to form a thin film via a CVD process by using the lanthanum compound according to the example embodiment, a liquid transporting method may be used. The liquid transporting method may include transporting the lanthanum compound in a liquid or solution state to the vaporizer 258, vaporizing the lanthanum compound in the vaporizer 258 by applying heat and/or reducing a pressure, and supplying the vaporized lanthanum compound into the reaction chamber 254. When the liquid transporting method is used, the lanthanum compound according to the example embodiment itself or a solution obtained by dissolving the lanthanum compound in an organic solvent may be used as a source compound for forming a thin film in the CVD process.

In some embodiments, a multi-component CVD process may be used to form a lanthanum-containing film in the method of forming the thin film according to the example embodiment. The multi-component CVD process may be performed by using a method (hereinafter, referred to as a "single source method") of independently vaporizing and supplying respective components of a source compound to be used in a CVD process or a method (hereinafter, referred to as a "cocktail source method") of vaporizing and supplying a mixed source obtained by previously mixing multi-component sources in a desired composition. When the cocktail source method is used, a first mixture containing the lanthanum compound according to the example embodiment, a first mixed solution obtained by dissolving the first mixture in an organic solvent, a second mixture containing the lanthanum compound according to the example embodiment and another precursor, or a second mixed solution obtained by dissolving the second mixture in an organic solvent may be used as a source compound for forming a thin film in a CVD process.

Organic solvents, which may be used to obtain the first mixed solution or the second mixed solution, may be or include acetate esters such as ethyl acetate, n-butyl acetate, and methoxyethyl acetate; ethers such as tetrahydrofuran, tetrahydropyran, ethylene glycol dimethyl ether, diethylene glycol dimethyl ether, triethylene glycol dimethyl ether, dibutyl ether, and dioxane; ketones such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons such as hexane, cyclohexane, methylcyclohexane, dimethylcyclohexane, ethylcyclohexane, heptane, octane, toluene, and xylene; hydrocarbons having a cyano group such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; pyridine; or lutidine. The above-described organic solvents may be used alone or in a mixture of at least two kinds thereof in consideration of relationships among solubilities, use temperatures, boiling points, and ignition points of solutes. When the organic solvent is used, the total amount of the lanthanum compound according to the example embodiment and another precursor may range from, for example, about 0.01 mol/L to about 2.0 mol/L, for example, about 0.05 mol/L to about 1.0 mol/L in the organic solvent.

When the multi-component CVD process is used to form the lanthanum-containing film in the method of forming the thin film according to the example embodiment, another precursor, which may be used together with the lanthanum compound according to the example embodiment, is not limited to specific kinds but may be one of precursors that may be used as a source compound in a CVD process.

In some embodiments, another precursor that may be used in a method of forming a thin film according to an example embodiment may include a compound of at least one organic coordination compound selected from the group of an alcohol compound, a glycol compound, a β-diketone compound, a cyclopentadiene compound, and an organic amine compound, and any one selected out of silicon and a metal. A metal forming the organic coordination compound may be magnesium (Mg), calcium (Ca), strontium (Sr), barium (Ba), titanium (Ti), zirconium (Zr), hafnium (Hf), vanadium (V), niobium (Nb), tantalum (Ta), manganese (Mn), palladium (Pd), platinum (Pt), copper (Cu), silver (Ag), gold (Au), zinc (Zn), aluminum (Al), gallium (Ga), indium (In), germanium (Ge), tin (Sn), lead (Pb), antimony (Sb), bismuth (Bi), yttrium (Y), nickel (Ni), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tin), ytterbium (Yb), etc.

The alcohol compound that may be used as the organic coordination compound of the another precursor may be, for example, alkyl-alcohols such as methanol, ethanol, propanol, isopropyl alcohol, butanol, sec-butyl alcohol, isobutyl alcohol, tert-butyl alcohol, pentyl alcohol, isopentyl alcohol, 3-pentyl alcohol; ether-alcohols such as 2-methoxyethanol, 2-ethoxyethanol, 2-butoxyethanol, 2-(2-methoxyethoxy)ethanol, 2-methoxy-1-methylethanol, 2-methoxy-1,1-dimethylethanol, 2-ethoxy-1,1-dimethylethanol, 2-propoxy-1,1-diethylethanol, 2-butoxy-1,1-diethylethanol, 2-(2-methoxyethoxy)-1,1-dimethylethanol, 2-propoxy-1,1-diethylethanol, 2-s-butoxy-1,1-diethylethanol, and 3-methoxy-1,1-dimethylpropanol; and dialkylaminoalcohol, etc.

A glycol compound, which may be used as the organic coordination compound of the another precursor, may be, for example, 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, 2,4-hexanediol, 2,4-dimethyl-2,4-pentanediol, etc.

The β-diketone compound that may be used as the organic coordination compound of the another precursor may be, for example, alkyl-substituted β-diketones such as acetylacetone, hexane-2,4-dione, 5-methylhexane-2,4-dione, heptane-2,4-dione, 2-methylheptane-3,5-dione, 5-methylheptane-2,4-dione, 6-methylheptane-2,4-dione, 2,2-dimethylheptane-3,5-dione, 2,6-dimethylheptane-3,5-dione, 2,2,6-trimethylheptane-3,5-dione, 2,2,6,6-tetramethylheptane-3,5-dione, octane-2,4-dione, 2,2,6-trimethyloctane-3,5-dione, 2,6-dimethyloctane-3,5-dione, 2,9-dimethylnonane-4,6-dione, 2-methyl-6-ethyldecane-3,5-dione, and 2,2-dimethyl-6-ethyldecane-3,5-dione; fluorine-substituted alkyl β-diketones such as 1,1,1-trifluoropentane-2,4-dione, 1,1,1-trifluoro-5,5-dimethylhexane-2,4-dione, 1,1,1,5,5,5-hexafluoropentane-2,4-dione, and 1,3-diperfluorohexylpropane-1,3-dione; and ether-substituted β-diketones such as 1,1,5,5-tetramethyl-1-methoxyhexane-2,4-dione, 2,2,6,6-tetramethyl-1-methoxyheptane-3,5-dione, 2,2,6,6-tetramethyl-1-(2-methoxyethoxy)heptane-3,5-dione, etc.

The cyclopentadiene compound that may be used as the organic coordination compound of the another precursor may be, for example, cyclopentadiene, methylcyclopentadiene, ethylcyclopentadiene, propylcyclopentadiene, isopropylcyclopentadiene, butylcyclopentadiene, sec-butylcyclopentadiene, isobutylcyclopentadiene, tert-butylcyclepentadiene, dimethylcyclopentadiene, tetramethylcyclopentadiene, etc.

The organic amine compound that may be used as the organic coordination compound of the another precursor may be, for example, methylamine, ethylamine, propylamine, isopropylamine, dimethylamine, diethylamine, dipropylamine, diisopropylamine, ethylmethylamine, propylmethylamine, isopropylmethylamine, etc.

In the method of forming the thin film according to the example embodiment, vapor obtained by vaporizing the lanthanum compound according to the example embodiment or a mixture of the lanthanum compound and another precursor may be supplied onto a substrate together with a reactive gas that is used as needed. Thus, the lanthanum-containing film may be grown and deposited on the substrate by continuously decomposing and/or reacting precursors on the substrate in accordance with a CVD process.

In the method of forming the thin film according to the example embodiment, a method of transporting a source compound, a deposition method, synthesis conditions, and synthesis equipment may be suitably selected.

The reactive gas that may be used in a method of forming a thin film according to an example embodiment may include an oxidizing gas, a reducing gas, or a nitrogen-containing gas.

The oxidizing gas may be or include, for example, oxygen, ozone, nitrogen dioxide, nitrogen monoxide, water vapor, hydrogen peroxide, formic acid, nitric acid, or acetic acid.

The reducing gas may be or include, for example, hydrogen, ammonia, or an organic metal compound.

The nitrogen-containing gas may be, for example, an organic amine compound (e.g., monoalkylamine, dialkylamine, trialkylamine, and alkylenediamine), hydrazine, or ammonia.

In the method of forming the thin film according to the example embodiment, a vapor transporting method, a liquid transporting method, a single source method, or a cocktail source method may be used to supply the source compound to the reaction chamber 254.

In the method of forming the thin film according to the example embodiment, the lanthanum-containing film may be formed by using a thermal CVD process of forming a thin film by reacting the vaporized source compound or both the vaporized source compound and a reactive gas due to heat, a plasma CVD process of forming a thin film by using heat and plasma, a photo-CVD process of forming a thin film by using heat and light, a photo-plasma CVD process of forming a thin film by using heat, light, and plasma, an ALD process of depositing a thin film by stages on a molecular level, etc.

In the method of forming the thin film according to the example embodiment, thin-film forming conditions for forming the lanthanum-containing film may include a reaction temperature (or substrate temperature), a reaction pressure, and a deposition speed.

The reaction temperature may be a temperature at which a lanthanum compound according to an example embodiment, for example, a lanthanum compound having a structure of Chemical Formula 2, may sufficiently react. In an example, the reaction temperature may be, for example, a temperature of about 100° C. or higher. In another example, the reaction temperature may be selected in the range of, for example about 150° C. to about 500° C.

The reaction pressure may be selected in the range of, for example, atmospheric pressure to about 10 Pa in a thermal CVD process or a photo-CVD process.

In addition, a deposition speed may be controlled by adjusting conditions (e.g., a vaporization temperature and a vaporization pressure) for supplying a source compound, a reaction temperature, and a reaction pressure. In the method of forming the thin film according to the example embodiment, a deposition speed of the lanthanum-containing film may be selected in the range of for example, about 0.01 nm/min to about 5000 nm/min, for example, in the range of about 0.1 nm/min to about 1000 nm/min.

When the lanthanum-containing film is formed by using an ALD process, the number of cycles of ALD processes may be adjusted to control a thickness of the lanthanum-containing film.

When the lanthanum oxide film is formed by using the ALD process, energy (e.g., plasma, light, or voltage) may be applied. Time points at which the energy is applied may be variously selected. For example, energy (e.g., plasma, light, or voltage) may be applied at a time point when a source gas containing the lanthanum compound is introduced into the reaction chamber 254, a time point when the source gas is adsorbed on the substrate, when an exhaust process is performed by using a purge gas, a time point when a reactive gas is introduced into the reaction chamber 254, or between the respective time points.

In the method of forming the thin film according to the example embodiment, after the lanthanum-containing film is formed by using the lanthanum compound having the structure of Chemical Formula 2, a process of heat-treating the lanthanum-containing film in an inert gas atmosphere, an oxidizing atmosphere, or a reducing atmosphere may be further performed. In an implementation, to remove a roughness from the surface of the lanthanum-containing film, a reflow process may be performed on the lanthanum-containing film. Each of the heat treatment and the reflow process may be performed under temperature conditions selected in the range of for example, about 250° C. to about 1000° C., for example, about 300° C. to about 500° C.

In the method of forming the thin film according to the example embodiment, various kinds of lanthanum-containing films may be formed by appropriately selecting a source compound according to an example embodiment, another precursor used together with the source compound, a reactive gas, and thin-film forming conditions. In some embodiments, the lanthanum-containing film formed by using the method of forming the thin film according to the example embodiment may be a lanthanum oxide film, a lanthanum nitride film, a lanthanum silicide film, etc.

A thin film formed by using a material for forming a thin film including the lanthanum compound according to the example embodiment may be of a desired kind (e.g., a metal, oxide ceramic, nitride ceramic, or glass) by appropriately selecting precursors containing different components, a reactive gas, and thin-film forming conditions. For instance, the thin film may be a lanthanum oxide film (e.g., a $La_2O_3$ film), a lanthanum thin film, a La—Al compound oxide thin film, a La—Zr—Hf compound oxide thin film, a La—Si—Zr—Hf compound oxide thin film, a La—Ta—Nb compound oxide thin film, a La—Si—Ta—Nb compound oxide thin film, a La-doped ferroelectric compound oxide thin film, or a La-doped glass thin film.

A lanthanum-containing film formed by using the method of forming the thin film according to the example embodiment may be used for various purposes. For example, the lanthanum-containing film may be used for a gate dielectric film of a transistor, a conductive barrier film used for interconnections, a resistive film, a magnetic film, a barrier metal film for liquid crystals, a member for thin-film solar cells, a member for semiconductor equipment, a nanostructure, a hydrogen storage alloy, a microelectromechanical systems (MEMS) device, an actuator, etc.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, synthesis examples and estimation examples of the lanthanum compound according to the example embodiment will be described.

Synthesis Example 1

Synthesis of Lanthanum Compound 40 g of lanthanum tris(2-trimethylsilylamide) complex and 120 g of anhydrous toluene were put in a reaction flask in an argon (Ar) atmosphere, and 12.1 g of ethylcyclopentadiene was slowly dropped at room temperature into the reaction flask. Thereafter, the mixture was heated at a temperature of about 40° C. for about 5 hours and then heated at a temperature of about 60° C. for about 3 hours to cause a reaction. The resultant product was removed of solvent, and the resulting product was then sublimated and purified by heating the same to a temperature of about 150° C. under a reduced pressure of about 40 Pa. 20 g of anhydrous toluene was put in the reaction flask, and 5.5 g of diisopropyl acetamidine was further slowly dropped into the reaction flask at room temperature. The resultant product was heated at a temperature of about 50° C. for about 3 hours and removed of solvent. The resulting product was distilled and purified under a reduced pressure of about 30 Pa at a temperature of about 145° C. to about 160° C. to obtain 13.0 g of target product.

(1) Analysis of elements (analysis of metals: inductively coupled plasma-atomic emission spectroscopy (ICP-AES))

La: 29.8% (theoretical value: 29.78%), C: 56.7% (theoretical value: 56.65%), H: 7.3% (theoretical value: 7.56%), N: 6.2% (theoretical value: 6.01%)

(2) $^1$H-NMR (solvent: hexadeuterobenzene) (Chemical shift: multiplicity: number of hydrogens)

(0.985:d:12H), (1.235:t:6H), (1.496:s:3H), (2.588:q:4H), (3.297:m:2H), (6.161:d:8H)

(3) Thermal gravimetric analysis (TGA)

TGA (Ar 100 ml/min, heating rate of about 10° C./min, sample amount of about 9.771 mg)

50 mass % and a reduced temperature of about 267.5° C.

Figure 7:
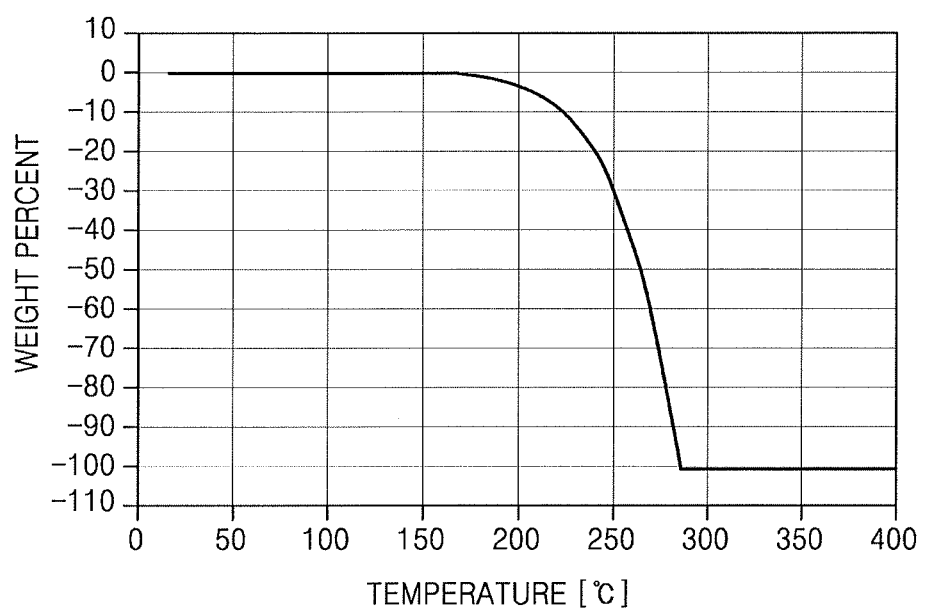
FIG. 7 illustrates a graph showing thermal gravimetric analysis (TGA) results of a lanthanum compound according to an example embodiment.

FIG. 7 is a graph showing thermal gravimetric analysis (TGA) results of the lanthanum compound obtained in Synthesis Example 1.

Figure 8:
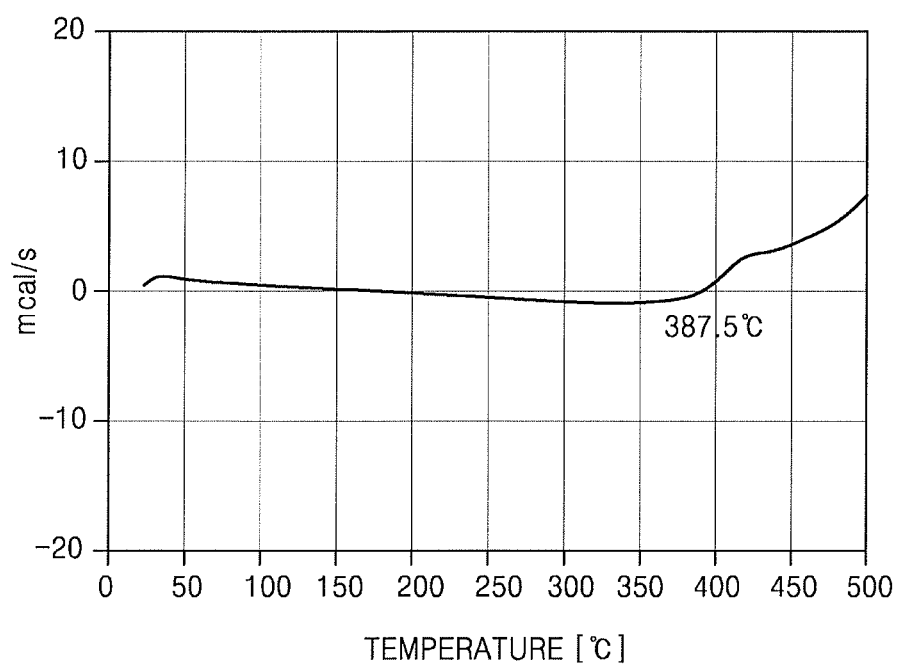
FIG. 8 illustrates a graph showing differential scanning calorimetry (DSC) analysis results of a lanthanum compound according to an example embodiment.

FIG. 8 is a graph showing differential scanning calorimetry (DSC) analysis results of the lanthanum compound obtained in Synthesis Example 1.

From the results of FIGS. 7 and 8, it can be seen that the lanthanum compound from Synthesis Example 1 has a relatively high decomposition temperature and good thermal stability.

Figure 9:
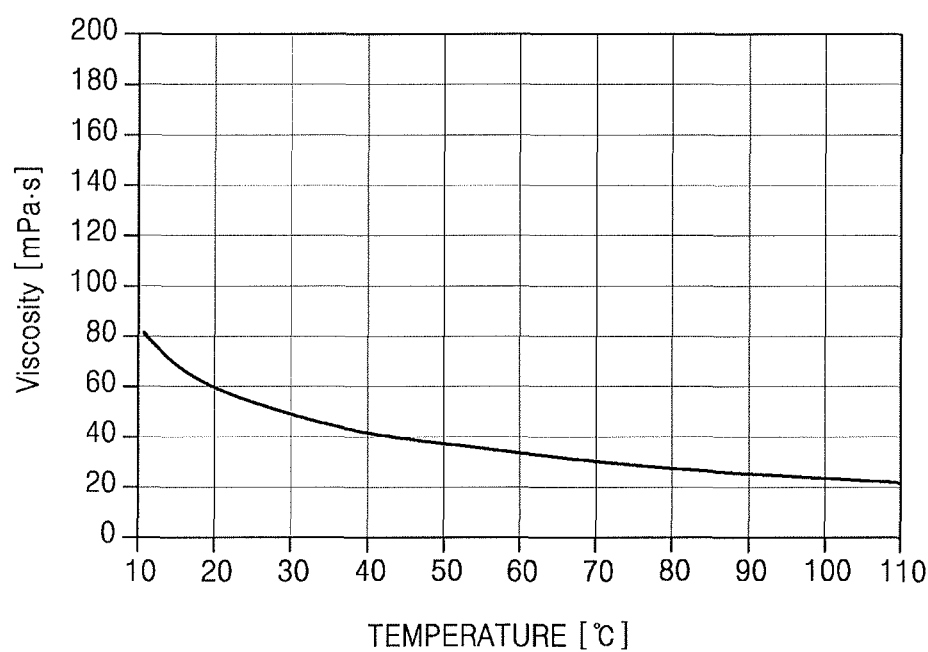
FIG. 9 illustrates a graph showing analysis results of viscosity of a lanthanum compound according to an example embodiment.

FIG. 9 is a graph showing analysis results of viscosity of the lanthanum compound obtained in Synthesis Example 1.

From the result in FIG. 9, it can be seen that the lanthanum compound from Synthesis Example 1 had a very low viscosity at room temperature. Accordingly, when the lanthanum compound from Synthesis Example 1 is used as a source gas in a thin-film deposition process, the lanthanum compound may be immediately vaporized, without an additional heat treatment for reducing viscosity, and supplied into a chamber configured to deposit a thin film.

Synthesis Example 2

Synthesis of Lanthanum Compound 40 g of lanthanum tris(2-trimethylsilylamide) complex and 120 g of anhydrous toluene were put in a reaction flask in an argon atmosphere, and 13.9 g of isopropylcyclopentadiene was slowly dropped at room temperature into the reaction flask. Thereafter, the mixture was heated at a temperature of about 40° C. for about 5 hours and then heated at a temperature of about 60° C. for about 3 hours to cause a reaction. The resultant product was removed of solvent, and the removed of solvent resultant product was then sublimated and purified by heating the same to a temperature of about 170° C. under a reduced pressure of about 40 Pa. 20 g of anhydrous toluene was put in the reaction flask, and 5.3 g of diisopropyl acetamidine was further slowly dropped into the reaction flask at room temperature. The resultant product was heated at a temperature of about 50° C. for about 3 hours and removed of solvent. The resultant product was distilled and purified under a reduced pressure of about 40 Pa at a temperature of about 160° C. to about 175° C. to obtain 14.1 g of target product.

(1) Analysis of elements (analysis of metals: ICP-AES)

La: 28.0% (theoretical value: 28.09%), C: 58.2% (theoretical value: 58.29%), H: 7.9% (theoretical value: 7.95%), N: 5.9% (theoretical value: 5.66%)

(2) $^1$H-NMR (solvent: hexadeuterobenzene) (Chemical shift: multiplicity: number of hydrogens)

(1.003:d:12H), (1.271:t:12H), (1.524:s:3H), (2.933:m:2H), (3.299:m:2H), (6.197:m:8H)

(3) TGA

TGA (Ar 100 ml/min, heating rate of about 10° C./min, sample amount of about 10.019 mg)

50 mass % and a reduced temperature of about 274.0° C.

Synthesis Example 3

Synthesis of Lanthanum Compound 40 g of lanthanum tris[bis(trimethylsilyl)amide] complex and 120 g of anhydrous toluene were put in a reaction flask in an argon atmosphere, and 13.9 g of isopropylcyclopentadiene was slowly dropped into the reaction flask at room temperature. Thereafter, the mixture was heated at a temperature of about 40° C. for about 5 hours and then heated at a temperature of about 60° C. for about 3 hours to cause a reaction. The resultant product was removed of solvent, and the removed of solvent resultant product was then sublimated and purified by heating the same to a temperature of about 170° C. under a reduced pressure of about 40 Pa. 20 g of anhydrous toluene was put in the reaction flask, and 6.6 g of ditertbutyl acetamidine was further slowly dropped into the reaction flask at room temperature. The resultant product was heated at a temperature of about 50° C. for about 3 hours and removed of solvent. The resultant product was distilled and purified under a reduced pressure of about 40 Pa at a temperature of about 175° C. to about 195° C. to obtain 15.1 g of target product.

(1) Analysis of elements (analysis of metals: ICP-AES)

La: 26.3% (theoretical value: 26.58%), C: 59.8% (theoretical value: 59.76%), H: 8.4% (theoretical value: 8.29%), N: 5.5% (theoretical value: 5.36%)

(2) $^1$H-NMR (solvent: hexadeuterobenzene) (Chemical shift: multiplicity: number of hydrogens)

(1.122:s:18H), (1.313:d:12H), (1.729:s:3H), (2.991:m:2H), (6.187:m:8H)

(3) TGA

TGA (Ar 100 ml/min, heating rate of about 10° C./min, sample amount of about 9.740 mg)

50 mass % and a reduced temperature of about 286.3° C.

Estimation Example

Formation of a Lanthanum Oxide Film

A lanthanum oxide film was formed on a silicon substrate via an ALD process using the lanthanum compound from Synthesis Example 1 as a material and using the deposition system 200A shown in FIG. 3.

In the present Estimation Example, the ALD process was performed at a reaction temperature (substrate temperature) of about 175° C. to about 425° C. by using gas obtained by mixing $O_3$ and $O_2$ in a mass ratio of 20:80 as a reactive gas.

To make the present estimation, one cycle including a series of processes (1) to (4) was repeated 100 times.

Figure 10:
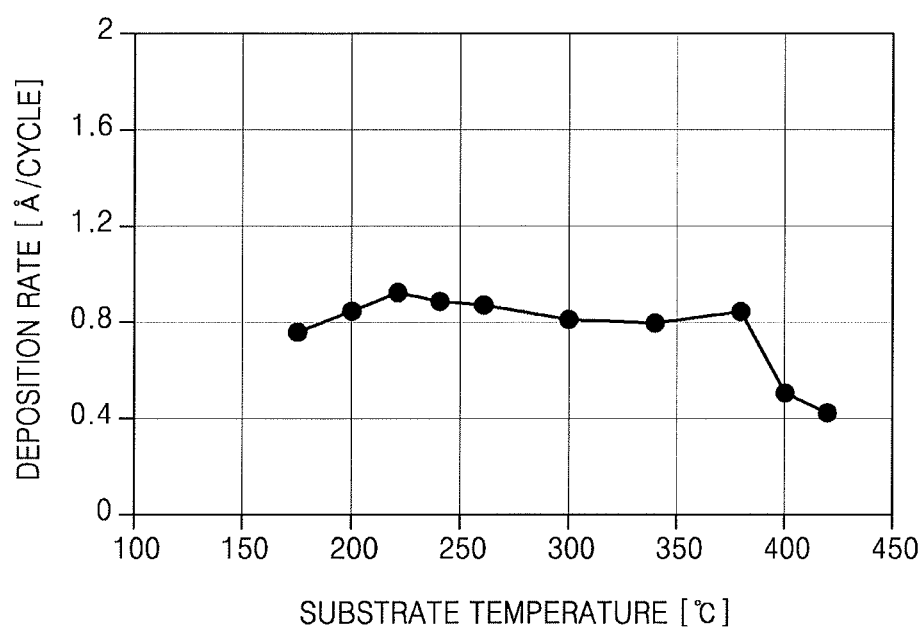
FIG. 10 illustrates a graph of a deposition rate relative to a deposition temperature in a process of forming a lanthanum oxide film by using a method of forming a thin film according to an example embodiment.

(1): a process of introducing the vaporized lanthanum compound from Synthesis Example 1 into a reaction chamber and adsorbing the vaporized lanthanum compound onto a substrate for about 10 seconds under a pressure of about 93 Pa (2): a process of performing a purge process using argon for about 10 seconds and removing unreacted sources from the reaction chamber (3): a process of introducing a reactive gas into the reaction chamber and causing a reaction for about 10 seconds under a pressure of about 93 Pa (4): a process of performing a purge process using argon for about 10 seconds and removing unreacted sources from the reaction chamber FIG. 10 is a graph of a deposition rate relative to a deposition temperature for forming a lanthanum oxide film in the above-described Estimation Example.

From the estimation results of FIG. 10, it can be seen that a stable ALD process may be performed at a temperature of about 150° C. to about 375° C.

Figure 11:
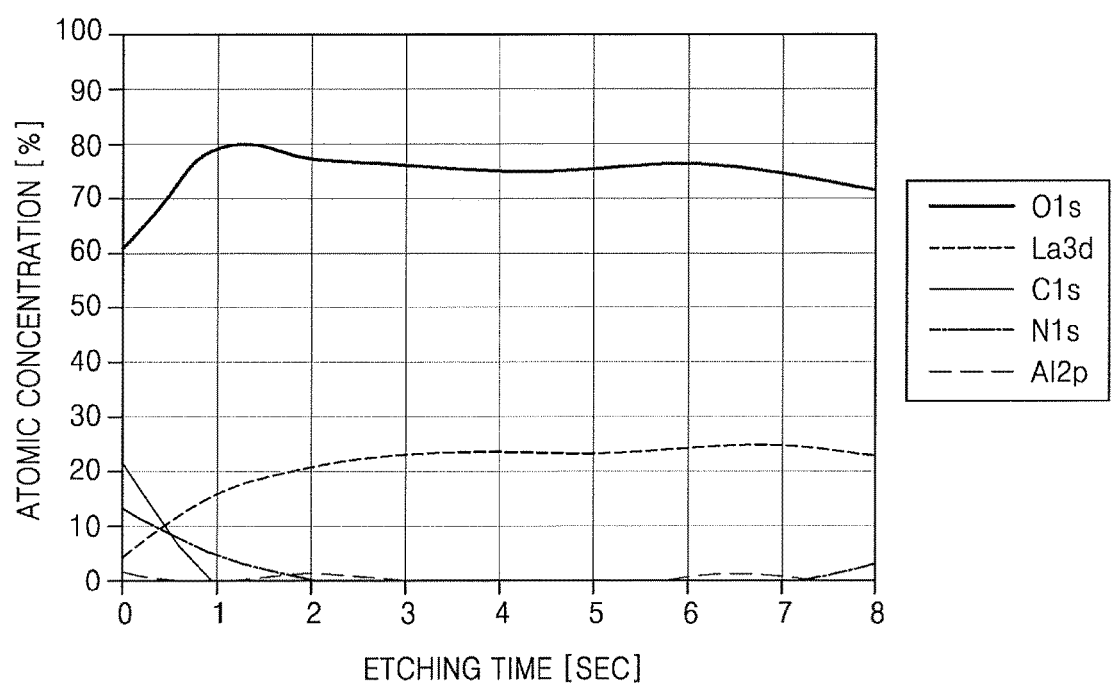
FIG. 11 illustrates an X-ray photoelectron spectroscopy (XPS) graph showing depth profile analysis results of a lanthanum oxide film that is obtained by using a method of forming a thin film according to an example embodiment.

FIG. 11 is an X-ray photoelectron spectroscopy (XPS) graph showing depth profile analysis results of a lanthanum oxide film that is obtained in the above-described Estimation Example.

FIG. 11 shows results obtained by confirming a structure and composition of a thin film of the resultant structure in which a lanthanum oxide film was formed on a substrate according to the Estimation Example and an $Al_2O_3$ capping film was formed on the lanthanum oxide film to a thickness of about 30 Å.

From the results of FIG. 11, it can be confirmed that all thin films obtained in the Estimation Example were lanthanum oxide films and a thickness of about 0.05 nm to about 0.1 nm was obtained per one cycle of the ALD process.

Figure 12A:
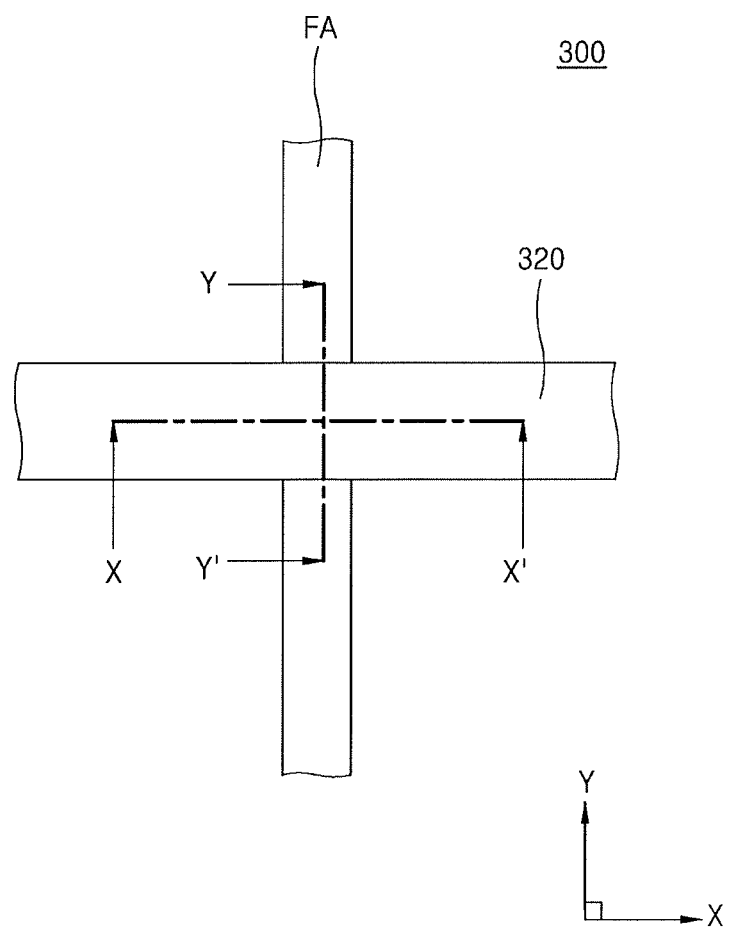
FIG. 12A illustrates a plan view of an IC device according to an example embodiment.
Figure 12B:
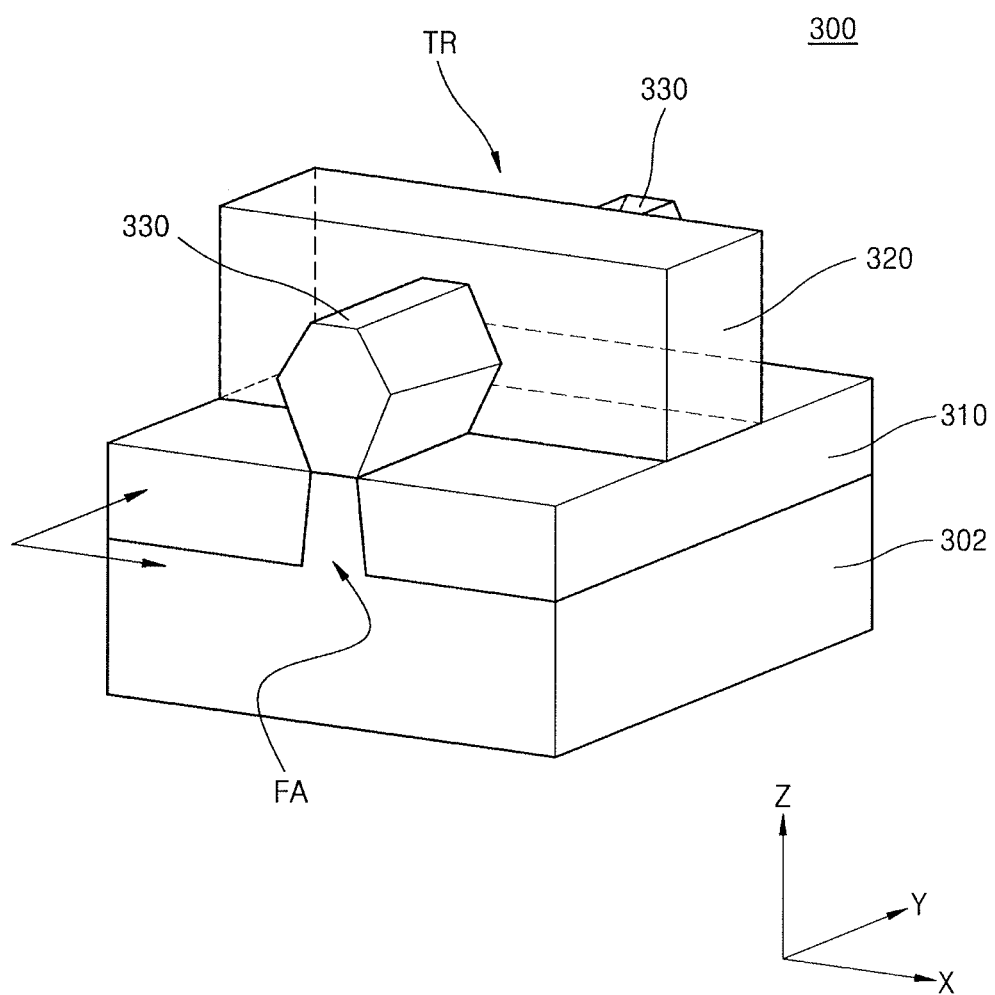
FIG. 12B illustrates a perspective view of the IC device of FIG. 12A.

FIG. 12A is a plan view of an IC device 300 according to an example embodiment, and FIG. 12B is a perspective view of the IC device 300 of FIG. 12A.

Referring to FIGS. 12A and 12B, the IC device 300 may include a fin-type active region FA protruding from a substrate 302.

The substrate 302 may include a semiconductor (e.g., silicon (Si) or germanium (Ge)) or a compound semiconductor (e.g., SiGe, SiC, GaAs, InAs, or InP). In some embodiments, the substrate 302 may be formed of at least one of a Group III-V material and a Group IV material. The Group III-V material may be a binary compound, ternary compound, or quaternary compound including at least one Group-III atom and at least one Group-V atom. The Group III-V material may be a compound including at least one Group-III atom and at least one Group-V atom. The at least one Group-III atom may be at least one atom of at least one of indium (In), gallium (Ga), and aluminum (Al), and the at least one Group-V atom may be at least one atom of arsenic (As), phosphorus (P), and antimony (Sb). For example, the Group III-V material may be selected from InP, $In_zGa_{1-z}As$ (0≤z≤1) and $Al_zGa_{1-z}As$ (0≤z≤1). The binary compound may be, for example, any one of InP, GaAs, InAs, InSb, and GaSb. The ternary compound may be any one of InGaP, InGaAs, AlInAs, InGaSb, GaAsSb, and GaAsP. The Group IV material may be silicon or germanium. However, a Group III-V material and a Group IV material, which may be used in an IC device according to an example embodiment, are not limited to the examples. The Group III-V material and the Group IV material (e.g., germanium) may be used as materials for forming channels of low-power high-speed transistors. A highly efficient CMOS device may be formed by using a semiconductor substrate formed of a Group III-V material (e.g., GaAs) having a higher electron mobility than a silicon substrate and a semiconductor substrate formed of a semiconductor material (e.g., Ge) having a higher hole mobility than the silicon substrate. In some embodiments, when an NMOS transistor is formed on the substrate 302, the substrate 302 may be formed of any one of the above-described Group III-V materials. In some other embodiments, when a PMOS transistor is formed on the substrate 302, the substrate 302 may be formed of germanium. In another example, the substrate 302 may have a silicon-on-insulator (SOI) structure. The substrate 302 may include a conductive region, for example, a doped well or a doped structure.

The fin-type active region FA may extend in one direction (refer to Y direction in FIGS. 12A and 12B). A device isolation layer 310 may be formed on the substrate 302 to cover lower sidewalls of the fin-type active region FA. The fin-type active region FA may protrude in a fin shape on the device isolation layer 310. In some embodiments, the device isolation layer 310 may include a silicon oxide film, a silicon nitride film, a silicon oxynitride film, a combination thereof, etc.

A gate structure 320 may be formed on the fin-type active region FA formed on the substrate 302, and extend in a direction (X direction) intersecting an extension direction of the fin-type active region FA. A pair of source and drain regions 330 may be formed on both sides of the gate structure 320 in the fin-type active region FA.

The one pair of source and drain regions 330 may include a semiconductor layer that may be epitaxially grown from the fin-type active region FA. Each of the one pair of source and drain regions 330 may include an embedded SiGe structure including a plurality of epitaxially grown SiGe layers, an epitaxially grown silicon layer, or an epitaxially grown SiC layer. FIG. 12B illustrates an example in which each of the one pair of source and drain regions 330 has a hexagonal sectional shape, but each of the one pair of source and drain regions 330 may have one of various shapes. For example, each of the one pair of source and drain regions 330 may have one of various sectional shapes, such as a circular shape, an elliptical shape, or a polygonal shape.

A MOS transistor TR may be formed at an intersection between the fin-type active region FA and the gate structure 320. The MOS transistor TR may include a three-dimensional (3D) MOS transistor having a channel formed on a top surface and both side surfaces of the fin-type active region FA. The MOS transistor TR may constitute an NMOS transistor or a PMOS transistor.

Figure 12C:
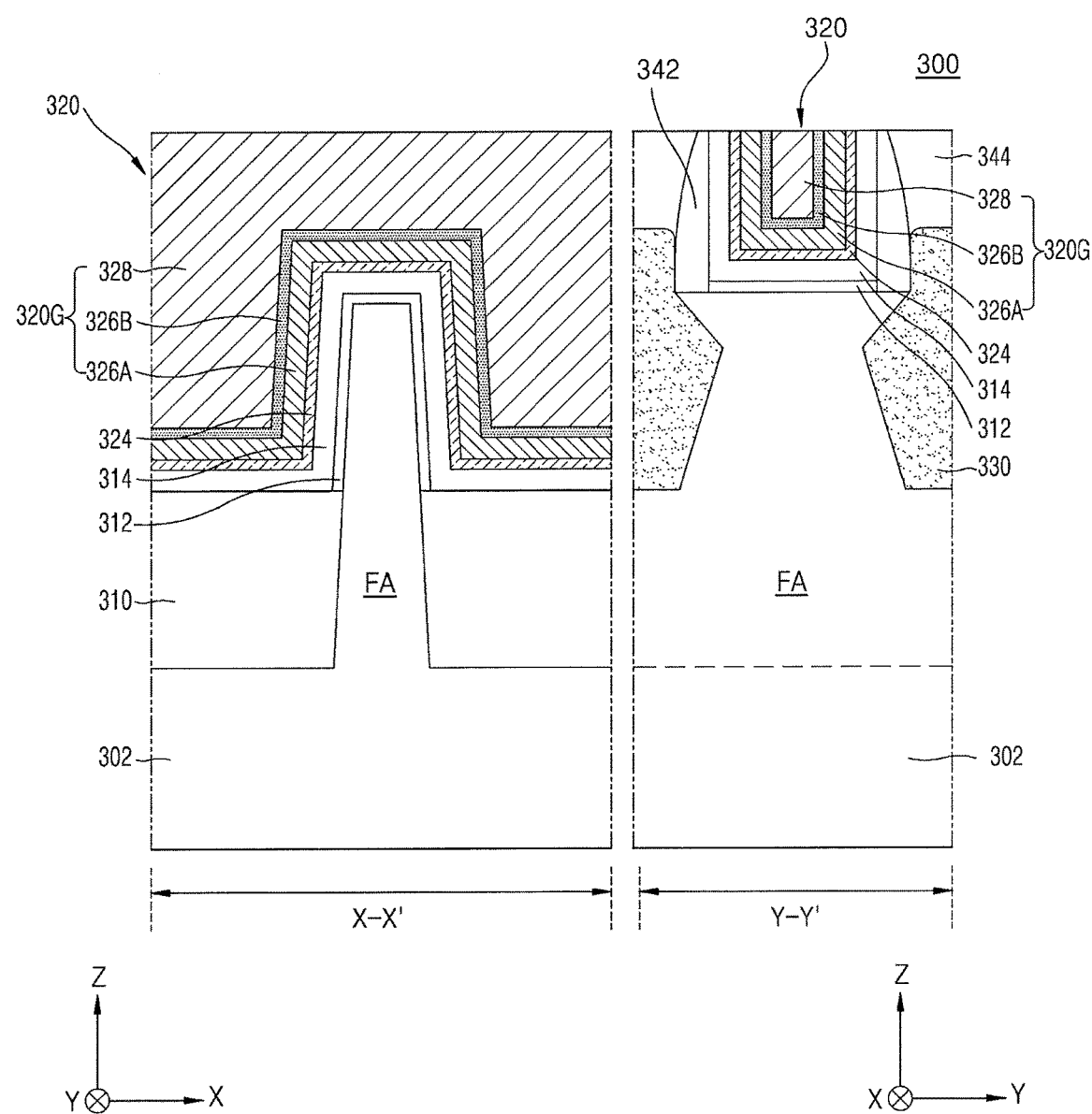
FIG. 12C illustrates cross-sectional views of the IC device of FIG. 12A.

FIG. 12C is a cross-sectional view taken along lines X-X' and Y-Y' of FIG. 12A.

Referring to FIG. 12C, the gate structure 320 may include an interface layer 312, a high-k dielectric film 314, a lanthanum-containing film 324, a first metal-containing layer 326A, a second metal-containing layer 326B, and a gap-fill metal layer 328, which are sequentially formed on the surface of the fin-type active region FA. In the gate structure 320, the first metal-containing layer 326A, the second metal-containing layer 326B, and the gap-fill metal layer 328 may constitute a gate electrode 320G.

Insulating spacers 342 may be formed on both side surfaces of the gate structure 320. An interlayer insulating layer 344 may be formed opposite the gate structure 320 across the insulating spacers 342 and cover the insulating spacers 342.

The interface layer 312 may be formed on the surface of the fin-type active region FA. The interface layer 312 may be formed of an insulating material, such as an oxide film, a nitride film, or an oxynitride film. The interface layer 312 and the high-k dielectric film 314 may constitute a gate insulating film.

The high-k dielectric film 314 may be formed of a material having a higher dielectric constant than a silicon oxide film. For example, the high-k dielectric film 314 may have a dielectric constant of about 10 to 25. The high-k dielectric film 314 may be formed of, for example, a material selected from the group of hafnium oxide, hafnium oxynitride, hafnium silicon oxide, zirconium oxide, zirconium silicon oxide, tantalum oxide, titanium oxide, barium strontium titanium oxide, barium titanium oxide, strontium titanium oxide, yttrium oxide, aluminum oxide, lead scandium tantalum oxide, and lead zinc niobate, a combination thereof, etc.

The high-k dielectric film 314 may be formed by using various deposition processes, such as an atomic layer deposition (ALD) process, a chemical vapor deposition (CVD) process, or a physical vapor deposition (PVD) process. Meanwhile, to subsequently control the amount of lanthanum atoms that subsequently diffuse from the lanthanum-containing film 324, a film structure and thickness of the high-k dielectric film 314 may be adjusted during the formation of the high-k dielectric film 314. Also, a heat treatment may be performed on the high-k dielectric film 314.

In some embodiments, the lanthanum-containing film 324 may include, for example, a $La_2O_3$ thin film.

As a method of controlling a threshold voltage Vth of a transistor, La atoms may be injected into an interface between the interface layer 312 and the high-k dielectric film 314. The lanthanum-containing film 324 may be used as a source of the La atoms to be injected into the interface between the interface layer 312 and the high-k dielectric film 314. La atoms may be supplied by using a diffusion process from the lanthanum-containing film 324 into the interface between the interface layer 312 and the high-k dielectric film 314. The La atoms in the interface between the interface layer 312 and the high-k dielectric film 314 may form a dipole with a material (e.g., $SiO_2$ or SiON) forming the interface layer 312, and vary a threshold voltage Vth of a transistor including the gate structure 320 and the fin-type active region FA.

The first metal-containing layer 326A may be formed to cover the lanthanum-containing film 324, and include titanium nitride, tantalum nitride, titanium oxynitride, or tantalum oxynitride. For example, the first metal-containing layer 326A may be formed of TiN, TaN, TiAlN, TaAlN, TiSiN, or a combination thereof.

The first metal-containing layer 326A may be formed by using various deposition methods, such as an ALD process, a CVD process, and a PVD process.

Furthermore, to adjust the amount of La atoms that diffuse from the lanthanum-containing film 324, a film structure, a composition of a metal component, a thickness, a process temperature, and a process time may be adjusted during the formation of the first metal-containing layer 326A. Also, a heat treatment may be performed after the first metal-containing layer 326A is formed.

The second metal-containing layer 326B may be formed on the first metal-containing layer 326A. The second metal-containing layer 326B and the first metal-containing layer 326A may function to adjust a work function of the gate structure 320. A threshold voltage of the gate structure 320 may be controlled by adjusting the work function of the gate structure 320 by using the first metal-containing layer 326A and the second metal-containing layer 326B.

In some embodiments, the second metal-containing layer 326B may include an N-type metal-containing layer required for an NMOS transistor including an aluminum (Al) compound containing titanium or tantalum. For example, the second metal-containing layer 326B may be formed of TiAlC, TiAlN, TiAlCN, TiAl, TaAlC, TaAlN, TaAlCN, TaAl, or a combination thereof.

In some other embodiments, the second metal-containing layer 326B may include a P-type metal-containing layer required for a PMOS transistor. For example, the second metal-containing layer 326B may include at least one of molybdenum (Mo), palladium (Pd), ruthenium (Ru), platinum (Pt), titanium nitride (TiN), tungsten nitride (WN), tantalum nitride (TaN), iridium (Ir), tantalum carbide (TaC), ruthenium nitride (RuN), and molybdenum nitride (MoN).

The second metal-containing layer 326B may include a single layer or a multilayered structure.

When the second metal-containing layer 326B includes aluminum, Al atoms may be injected by using a diffusion process from the second metal-containing layer 326B into the first metal-containing layer 326A. Thus, a work function of a transistor including the second metal-containing layer 326B may be controlled so that a threshold voltage of the transistor may be determined. In an implementation, the work function of the transistor may be adjusted by transporting electrons between the first metal-containing layer 326A and the second metal-containing layer 326B.

In some embodiments, the first metal-containing layer 326A may include La atoms, which may diffuse from the lanthanum-containing film 324. The La atoms injected into the first metal-containing layer 326A may affect the density of charges in the first metal-containing layer 326A and vary the threshold voltage of the transistor. The influence of the La atoms upon the density of charges may depend on the Al content or the amount of Al atoms in the first metal-containing layer 326A. For example, as the amount of Al atoms in the first metal-containing layer 326A increases, a difference in threshold voltage may increase depending on the presence or absence of La atoms.

The amount of La atoms injected into the interface between the interface layer 312 and the high-k dielectric film 314 may not be varied by a composition or content of an aluminum-containing material in the first metal-containing layer 326A. Accordingly, a threshold voltage may be varied without degrading reliability and performance of a semiconductor device.

When the gate structure 320 is formed by using a replacement metal gate (RMG) process, the gap-fill metal layer 328 may be formed to fill the remaining gate space formed on the second metal-containing layer 326B. After the second metal-containing layer 326B is formed, when there is no remaining gate space on the second metal-containing layer 326B, the gap-fill metal layer 328 may not be formed on the second metal-containing layer 326B but omitted.

The gap-fill metal layer 328 may include a material selected from the group of tungsten (W), a metal nitride (e.g., TiN and TaN), aluminum (Al), a metal carbide, a metal silicide, a metal aluminum carbide, a metal aluminum nitride, and a metal silicide nitride.

The IC device 300 shown in FIGS. 12A to 12C may include La atoms at an interface between the interface layer 312 and the high-k dielectric film 314. Also, the first metal-containing layer 326A disposed on the interface may contain La atoms. Thus, a transistor having a precisely controlled threshold voltage may be embodied.

Although an IC device including a fin field-effect transistor (FinFET) having a 3-dimensional channel has been described with reference to FIGS. 12A to 12C, embodiments may provide IC devices including planar metal-oxide-semiconductor FETs (MOSFETs) and methods of manufacturing the same by making suitable changes.

FIGS. 13A to 13G are cross-sectional views of process operations of a method of manufacturing the IC device shown in FIGS. 12A to 12C, according to an example embodiment.

FIGS. 13A to 13G are cross-sectional views corresponding to FIG. 12C, which is the cross-sectional view taken along the lines X-X' and Y-Y' of FIG. 12A. In FIGS. 13A to 13G, the same reference numerals are used to denote the same elements as in FIGS. 12A to 12C, and detailed descriptions thereof are omitted.

Figure 13A:
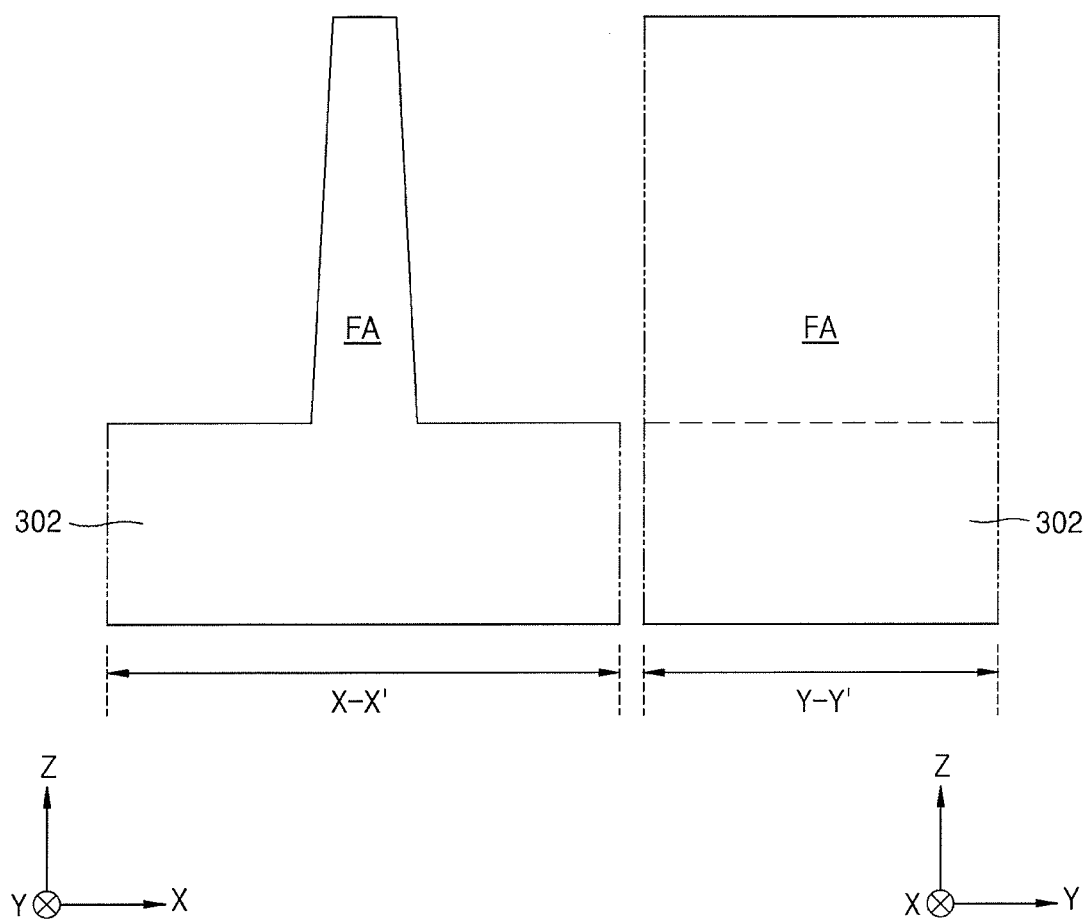

Referring to FIG. 13A, an upper portion of a substrate 302 may be partially etched to form a fin-type active region FA.

The fin-type active region FA may be configured to extend on the substrate 302 in one direction (Y direction).

Figure 13B:
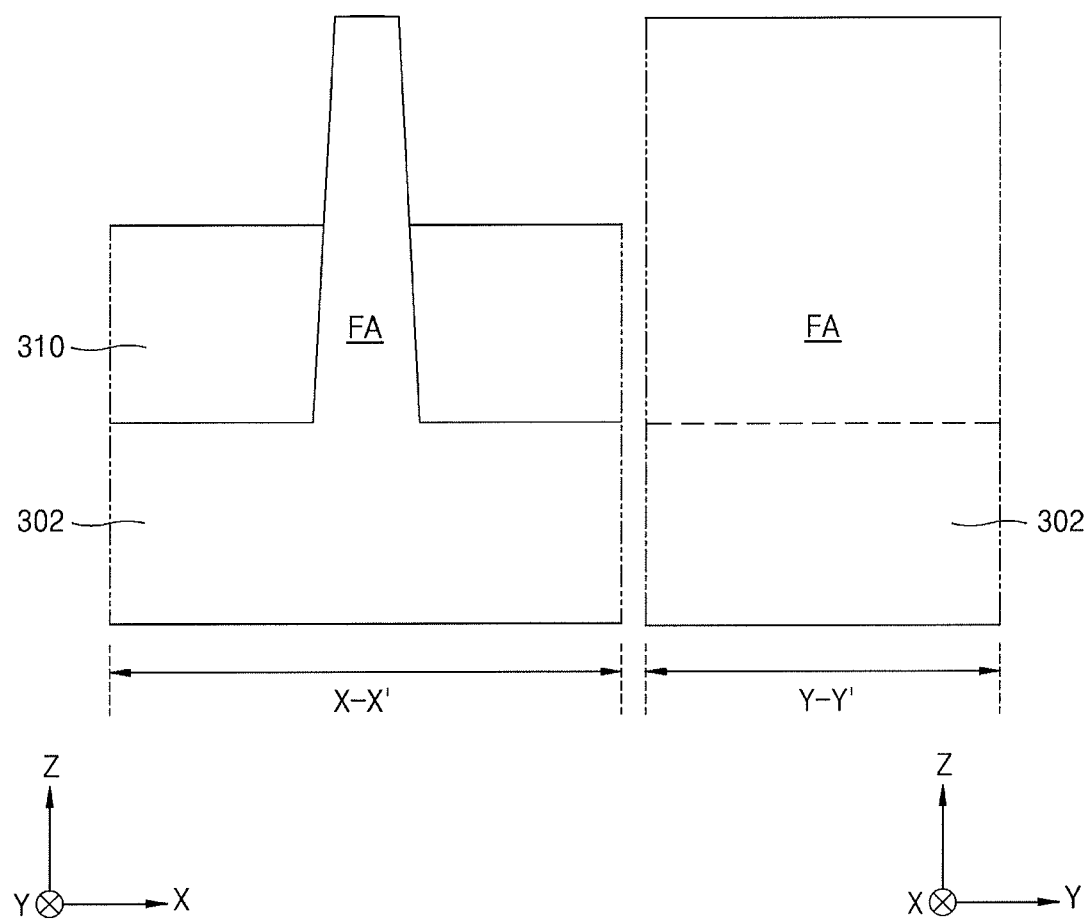

Referring to FIG. 13B, a device isolation layer 310 may be formed at a lower portion of the fin-type active region FA to cover both sidewalls of the fin-type active region FA.

After the device isolation layer 310 is formed, an upper portion of the fin-type active region FA may protrude from the device isolation layer 310.

Figure 13C:
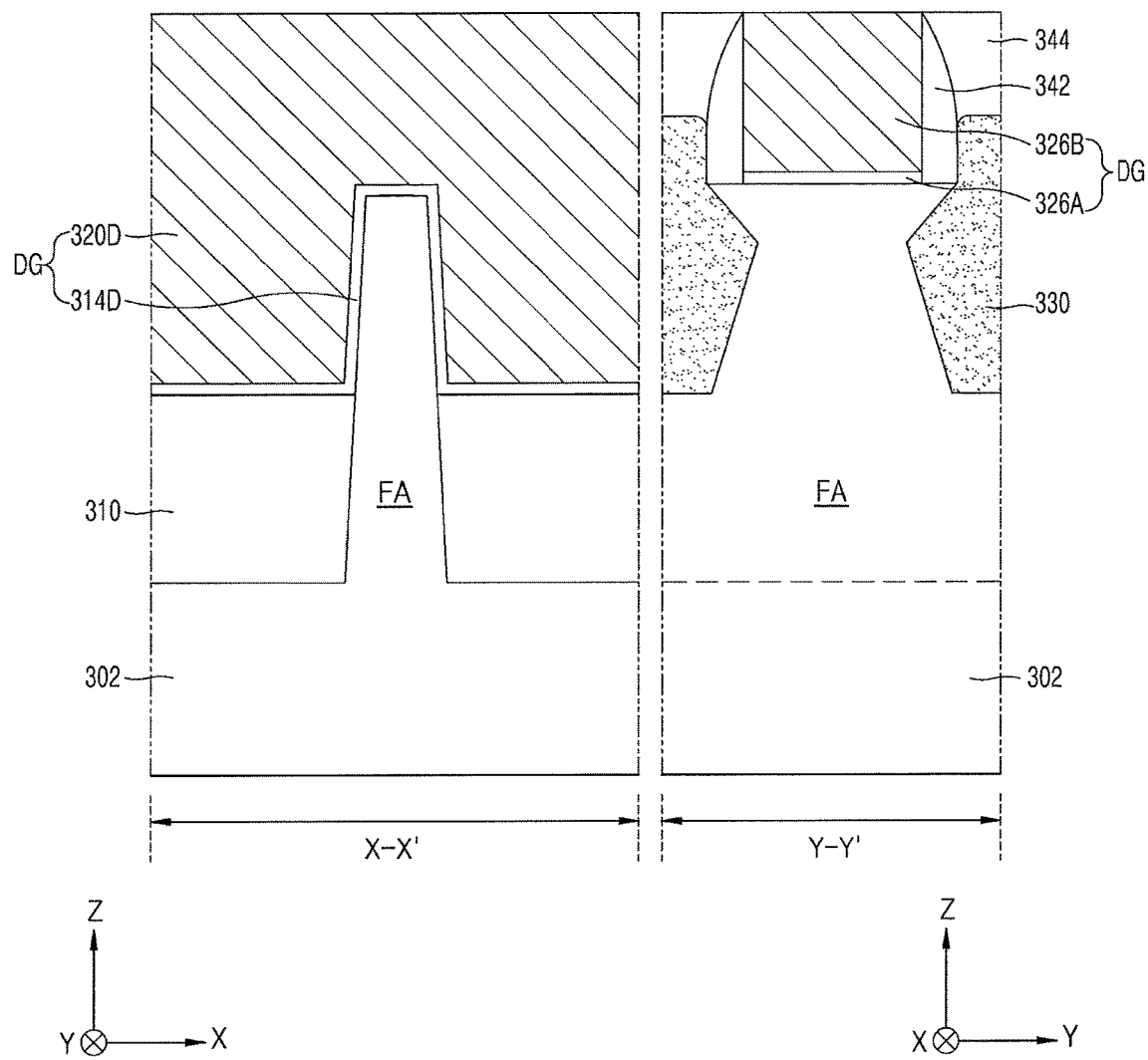

Referring to FIG. 13C, a dummy gate structure DG including a dummy gate insulating layer 314D and a dummy gate electrode 320D may be formed to cover the upper portion of the fin-type active region FA. Insulating spacers 342 may be formed to cover both sidewalls of the dummy gate structure DG. Thereafter, source and drain regions 330 (refer to FIG. 12B) may be formed in the fin-type active region FA on both sides of the dummy gate structure DG. An interlayer insulating film 344 may be formed on both sides of the dummy gate structure DG to cover the source and drain regions 330.

The dummy gate structure DG may extend in a direction (X direction) that intersects an extension direction of the fin-type active region FA.

In some embodiments, the dummy gate insulating layer 314D may include a silicon oxide film, the dummy gate electrode 320D may include poly-Si, and the insulating spacers 342 may include a silicon nitride film. The interlayer insulating film 344 may include a silicon oxide film, a silicon nitride film, or a combination thereof.

Figure 13D:
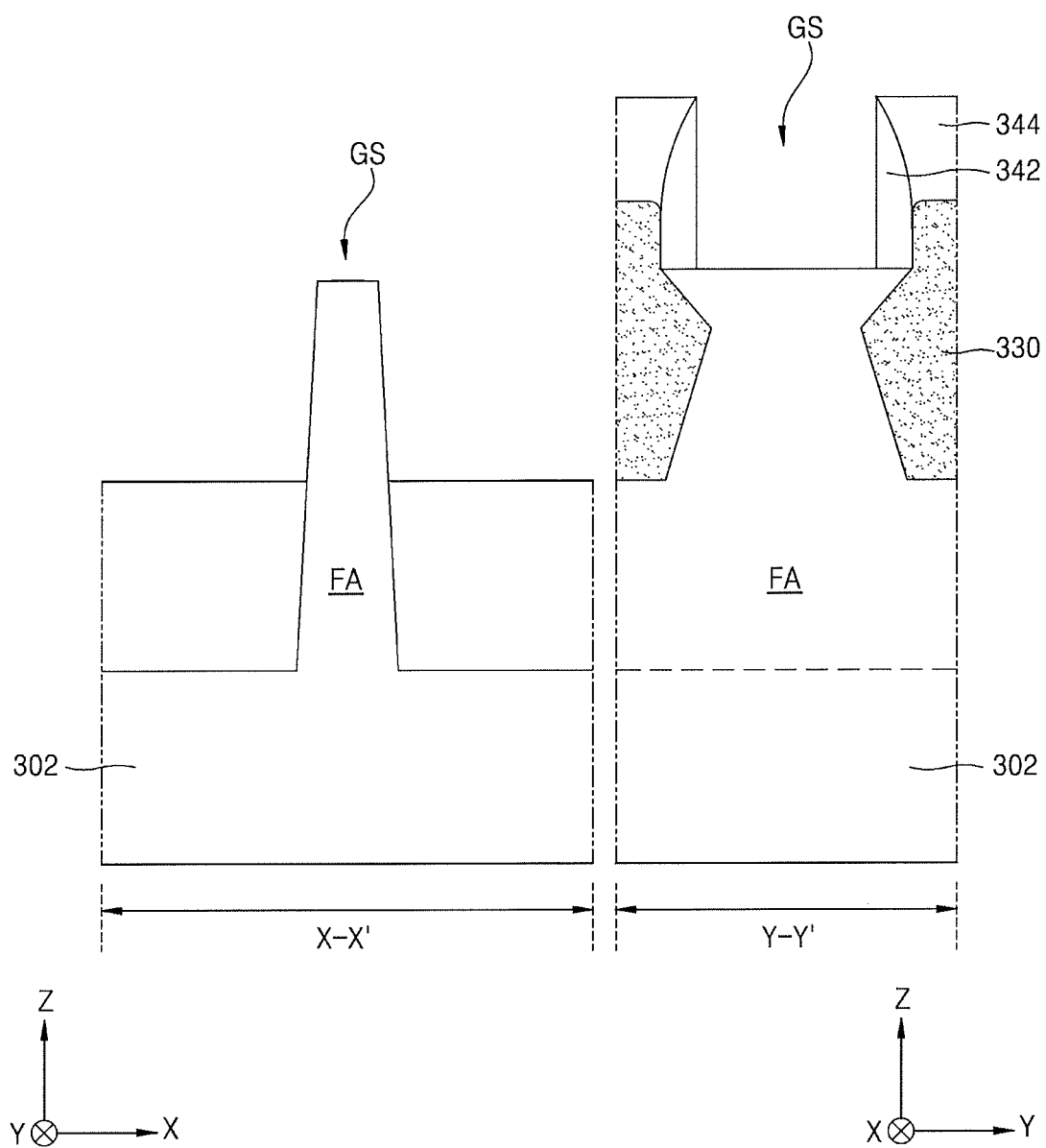

Referring to FIG. 13D, the dummy gate structure DG exposed by the interlayer insulating film 344 may be removed so that the fin-type active region FA may be exposed by a gate space GS between a pair of insulating spacers 342.

Figure 13E:
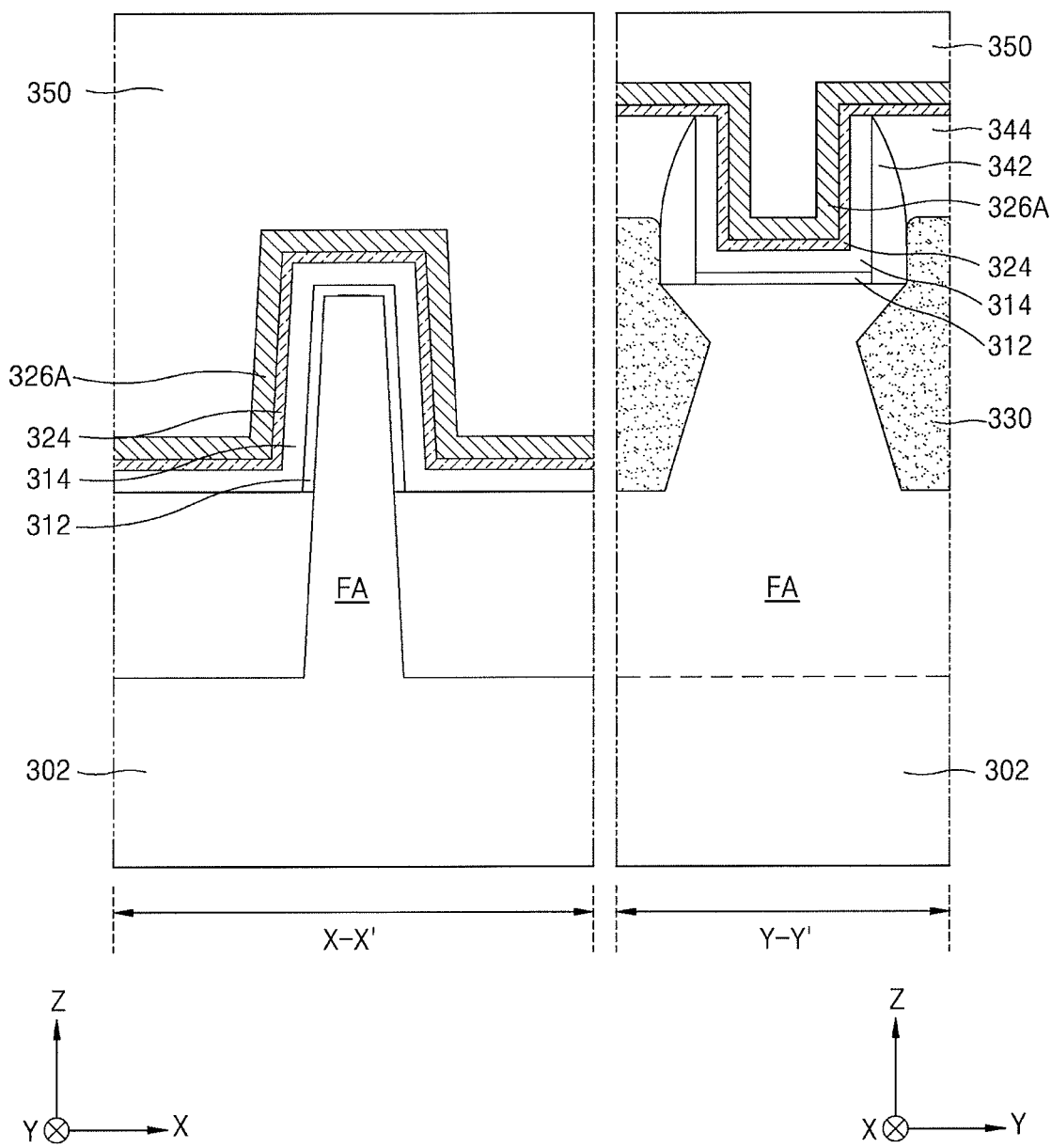

Referring to FIG. 13E, an interface layer 312 and a high-k dielectric film 314 may be sequentially formed on the surface of the fin-type active region FA exposed by the gate space GS. Thereafter, a lanthanum-containing film 324 may be formed on the high-k dielectric film 314 by using a lanthanum precursor composition containing the lanthanum compound having the structure of Chemical Formula 2, according to an example embodiment.

In some embodiments, the lanthanum-containing film 324 may be formed by using a lanthanum precursor composition formed of only the lanthanum compound CF-2 that is obtained by using the method described with reference to FIG. 1.

In some other embodiments, the lanthanum-containing film 324 may be formed by using a lanthanum precursor composition including the lanthanum compound CF-2, which is obtained by using the method described with reference to FIG. 1, and a silicon-containing compound. The silicon-containing compound may include the silicon-containing intermediate CF-1, which is a reactant of Reaction Equation 3. The silicon-containing compound may be contained at a content of, for example, about 10 ppb to about 100 ppb, based on the total weight of the lanthanum precursor composition.

Thereafter, a first metal-containing layer 326A may be formed on the lanthanum-containing film 324.

In some embodiments, a lanthanum-containing film 324 and a first metal-containing layer 326A may be formed on the high-k dielectric film 314 on other regions (not shown) of the substrate 302 during the formation of the lanthanum-containing film 324 and the first metal-containing layer 326A. The other regions may include regions that do not need the lanthanum-containing film 324 and the first metal-containing layer 326A. In this case, a mask pattern 350 may be formed to expose the regions, which do not need the lanthanum-containing film 324 and the first metal-containing layer 326A, and cover regions, which need the lanthanum-containing film 324 and the first metal-containing layer 326A. Unnecessary portions of the lanthanum-containing film 324 and the first metal-containing layer 326A may be removed by using the mask pattern 350 as an etch mask to expose the high-k dielectric film 314.

Referring to FIG. 13F, after the mask pattern 350 is removed from the resultant structure of FIG. 13E, the resultant structure in which the first metal-containing layer 326A is exposed by the gate space GS may be heat-treated (HT).

In some embodiments, the heat treatment (HT) may be performed at, for example, a temperature of about 400° C. to about 600° C. for about 5 minutes to one hour.

Due to the heat treatment (HT), La atoms may diffuse from the lanthanum-containing film 324 into an interface between the interface layer 312 and the high-k dielectric film 314.

The amount of La atoms that diffuse into the interface between the interface layer 312 and the high-k dielectric film 314 may be adjusted by using various methods based on the result of the heat treatment (HT). For example, the amount of La atoms in the interface between the interface layer 312 and the high-k dielectric film 314 may be adjusted by using a film quality and film thickness of the high-k dielectric film 314 and a heat-treatment (HT) temperature.

In some embodiments, the heat treatment (HT) described with reference to FIG. 13F may be omitted.

Figure 13G:
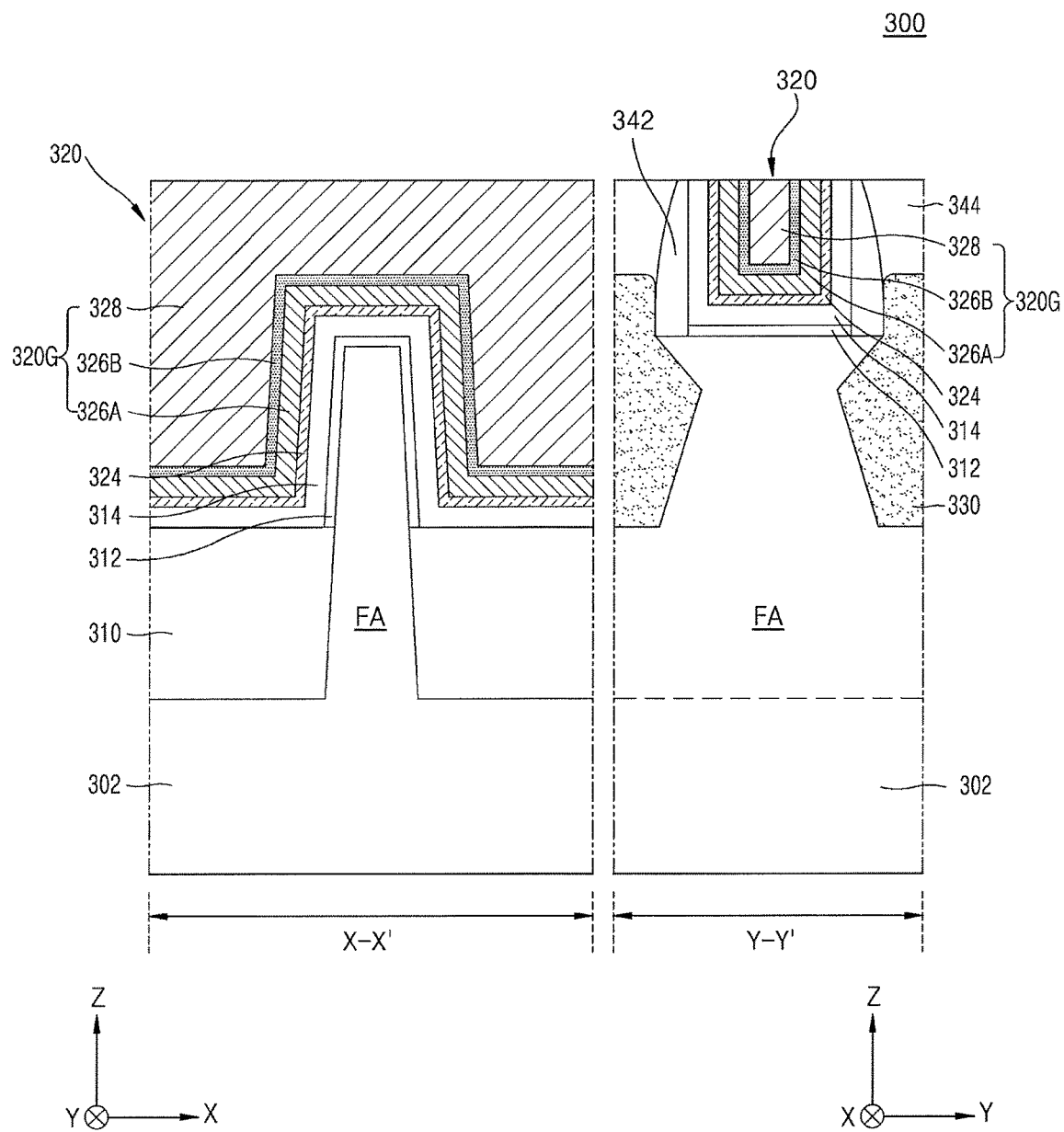

Referring to FIG. 13G, a second metal-containing layer 326B and a gap-fill metal layer 328 may be sequentially formed on the first metal-containing layer 326A exposed by the gate space GS. Thereafter, a planarization process (e.g., a chemical mechanical polishing (CMP) process) may be performed until a top surface of the interlayer insulating film 344 is exposed. Thus, the IC device 300 shown in FIGS. 12A to 12C may be completed.

In the method of manufacturing the IC device 300, which is described with reference to FIGS. 13A to 13G, La atoms may diffuse from the lanthanum-containing film 324 into the interface between the interface layer 312 and the high-k dielectric film 314. As a result, a threshold voltage of a transistor may be additionally changed due to the amount of the La atoms in the interface between the interface layer 312 and the high-k dielectric film 314. Thus, the IC device 300 may further include a unit configured to control a threshold voltage so that a precisely controlled threshold voltage may be provided and reliability of the IC device 300 may increase.

Furthermore, the lanthanum-containing film 324 described with reference to FIG. 13E may be formed via an ALD process using the lanthanum compound having the structure of Chemical Formula 2, according to the example embodiment, as a precursor. In the ALD process for forming the lanthanum-containing film 324, the lanthanum compound having the structure of Chemical Formula 2, according to the example embodiment, may provide characteristics required for a source compound of an ALD process, for example, a low melting point, a high vapor pressure, transportability in a liquid state, ease of vaporization, and a high thermal stability. Accordingly, it may be easy to perform the process of forming the lanthanum-containing film 324 by using the lanthanum compound having the structure of Chemical Formula 2, according to the example embodiment.

Figure 14:
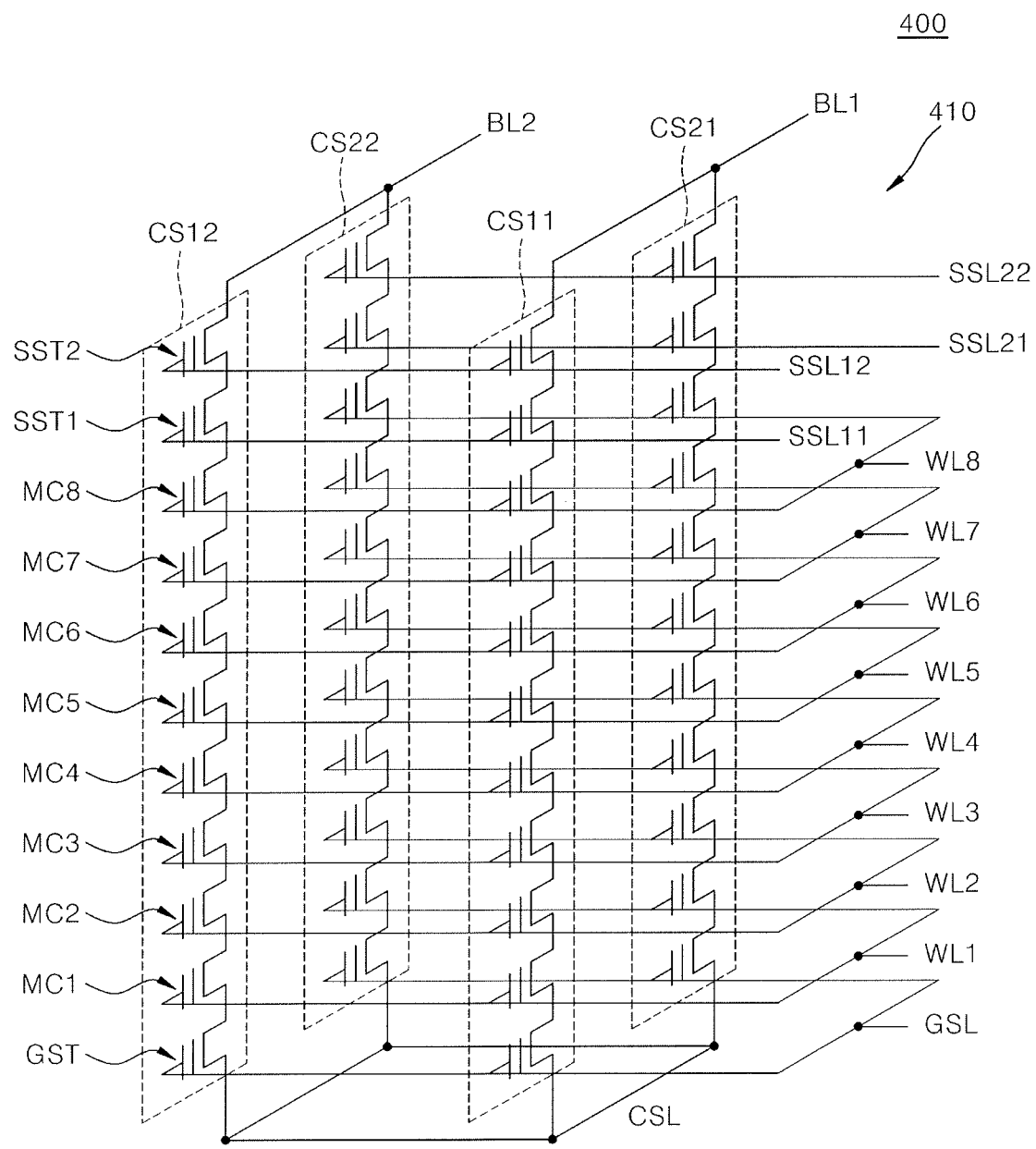
FIG. 14 illustrates an equivalent circuit diagram of an IC device according to another example embodiment.

FIG. 14 is an equivalent circuit diagram of an IC device 400 according to another example embodiment. FIG. 14 is an equivalent circuit diagram of a vertical NAND (VNAND) flash memory device having a vertical channel structure.

A memory cell array 410 may have a 3D structure. The memory cell array 410 may include a plurality of cell strings CS11, CS12, CS21, and CS22 that may extend in a vertical direction. Each of the cell strings CS11, CS12, CS21, and CS22 may include a ground selection transistor GST, a plurality of memory cell transistors MC1, MC2, . . . , and MC8, and string selection transistors SST1 and SST2, which are connected in series. Although FIG. 10 illustrates an example in which one ground selection transistor GST and two string selection transistors SST1 and SST2 are connected to the plurality of cell strings CS11, CS12, CS21, and CS22, the number of ground selection transistors GST connected to the cell strings CS11, CS12, CS21, and CS22 and the number of string selection transistors SST1 and SST2 connected to the cell strings CS11, CS12, CS21, and CS22 are not limited thereto. Also, the number of the plurality of memory cell transistors MC1, MC2, . . . , and MC8 is not limited to the example.

The string selection transistors SST1 and SST2 of each of the plurality of cell strings CS11, CS12, CS21, and CS22 may be connected to bit lines BL1 and BL2 corresponding thereto. Also, string selection transistors SST1 and SST2 of each of the plurality of cell strings CS11, CS12, CS21, and CS22 may be connected to string selection lines SSL11, SSL12, SSL21, and SSL22. The ground selection transistors UST of the plurality of cell strings CS11, CS12, CS21, and CS22 may be connected by ground selection lines GSL. A common source line CSL may be connected to the ground selection transistor GST of each of the cell strings CS11, CS12, CS21, and CS22.

The plurality of memory cell transistor MC1, MC2, . . . , and MC8 disposed at the same level may be connected to the same gate lines WL1, WL2, . . . , and WL8. For example, a first memory cell transistor MC1 connected to the ground selection transistor GST may be connected to first memory cell transistors MC of adjacent columns through the gate line WL1.

The IC device 400 shown in FIG. 14 may include a lanthanum-containing film, which is obtained by using the lanthanum compound having the structure of Chemical Formula 2, according to the example embodiment.

Figure 15:
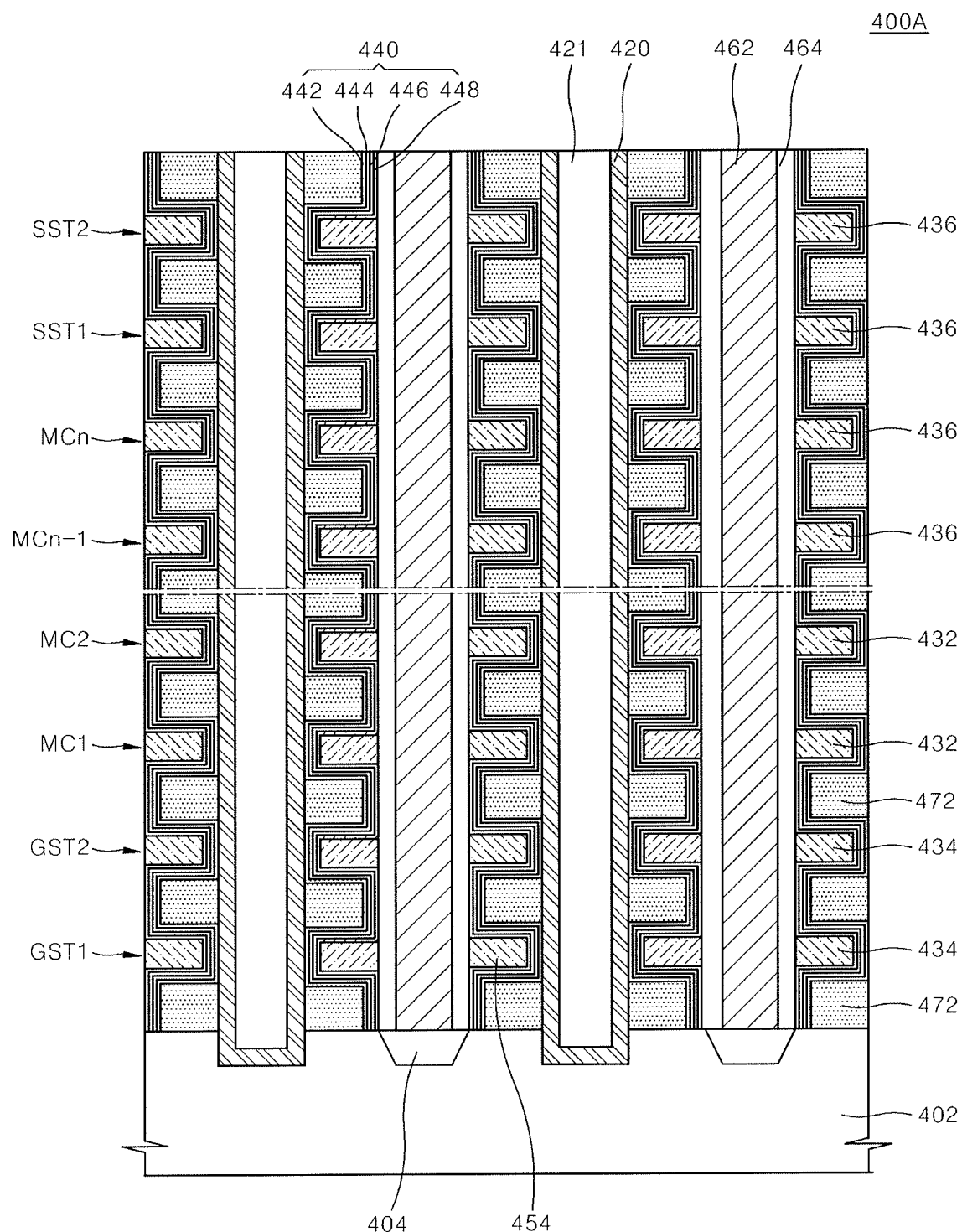
FIG. 15 illustrates a perspective view of some elements of a non-volatile memory device including a lanthanum-containing film formed by using a method of forming a thin film according to an example embodiment.

FIG. 15 is a diagram of an example of an IC device including a lanthanum-containing film according to an example embodiment. FIG. 15 is a sectional view of some elements of an example of a non-volatile memory device 400A that may constitute the memory cell array 410 of the IC device 400 shown in FIG. 14. The bit lines BL1 and BL2 shown in FIG. 14 are omitted in FIG. 15.

Referring to FIG. 15, the non-volatile memory device 400A may include ground selection transistors GST1 and GST2, a plurality of memory cells MC1, MC2, . . . , and MCn, and string selection transistors SST1 and SST2, which may be sequentially formed on a substrate 402. An insulating layer 472 may be provided among the ground selection transistors GST1 and GST2, the plurality of memory cells MC1, MC2, . . . , and MCn, and the string selection transistors SST1 and SST2.

Detailed descriptions of the substrate 402 may be substantially the same as those of the substrate 302 presented with reference to FIGS. 12A to 12C.

A channel layer 420 may vertically extend on a partial region of the substrate 402. First to third control gate electrodes 432, 434, and 436, which may constitute the plurality of memory cells MC1, MC2, . . . , and MCn, the ground selection transistors GST1 and GST2, and the string selection transistors SST1 and SST2, may be arranged along sidewalls of the channel layer 420.

A storage structure 440 may be interposed between the first to third control gate electrodes 432, 434, and 436 and the channel layer 420. The storage structure 440 may continuously extend along surfaces of the first to third control gate electrode 432, 434, and 436. The inside of the channel layer 420 may be filled with a buried insulating film 421.

The storage structure 440 may include a lanthanum-containing film 448, which is obtained by using the lanthanum compound having the structure of Chemical Formula 2, according to the example embodiment. FIG. 15 illustrates a case in which the storage structure 440 includes a tunneling insulating layer 442, a charge storage layer 444, a blocking insulating layer 446, and a lanthanum-containing film 448, which are sequentially stacked on the surface of the channel layer 420, but the stacked order thereof is not limited thereto. The storage structure 440 may function as a gate insulating film.

In some embodiments, the tunneling insulating layer 442 may be formed of silicon oxide, the charge storage layer 444 may be formed of silicon nitride, the blocking insulating layer 446 may be formed of aluminum oxide, and the lanthanum-containing film 448 may be formed of $La_2O_3$, but materials forming the storage structure 440 are not limited to the examples.

Each of the plurality of memory cells MC1, MC2, . . . , and MCn may include a first control gate electrode 432, which may be electrically connected to the storage structure 440. Each of the ground selection transistors GST1 and GST2 may include a second control gate electrode 434 that may be electrically connected to the storage structure 440. Each of the string selection transistors SST1 and SST2 may include a third control gate electrode 436 that may be electrically connected to the storage structure 440.

Each of the first to third control gate electrodes 432, 434, and 436 may include a conductive barrier film, which may be in contact with the lanthanum-containing film 448 of the storage structure 440, and a conductive film formed on the conductive barrier film. The conductive film may include conductive poly-Si, a metal, a metal silicide, or a combination thereof. For example, the conductive film may be formed of titanium silicide, tantalum silicide, tungsten silicide, cobalt silicide, or lanthanum silicide.

A common source line 462 may be formed on a source region 404 formed in an upper region of the substrate 402. The ground selection transistors GST1 and GST2, the plurality of memory cells MC1 MC2, . . . , and MCn, and the string selection transistors SST1 and SST2 may be located between the channel region 420 and the common source line 462. Sidewalls of the common source line 462 may be covered with insulating spacers 464.

In the non-volatile memory device 400A shown in FIG. 15, the storage structure 440 may include a lanthanum-containing film 448, which may be interposed between the blocking insulating layer 446 and the first to third control gate electrodes 432, 434, and 436. Thus, since the storage structure 440 includes the lanthanum-containing film 448 that includes a high-k dielectric film, reliability of the IC device may be improved.

In the non-volatile memory device 400A shown in FIG. 15, the lanthanum-containing film 448 included in the storage structure 440 may be formed via an ALD process using the lanthanum compound having the structure of Chemical Formula 2, according to the example embodiment.

In some embodiments, the lanthanum-containing film 448 may be formed by using the lanthanum precursor composition including only the lanthanum compound CF-2, which is obtained by using the method described with reference to FIG. 1.

In some other embodiments, the lanthanum-containing film 448 may be formed by using a lanthanum precursor composition including the lanthanum compound CF-2, which is obtained by using the method described with reference to FIG. 1, and a silicon-containing compound. The silicon-containing compound may include the silicon-containing intermediate CF-1, which is the reactant of Reaction Equation 3. The silicon-containing compound may be contained at a content of, for example, about 10 ppb to about 100 ppb, based on the total weight of the lanthanum precursor composition.

In the ALD process for forming the lanthanum-containing film 448, the lanthanum compound having the structure of Chemical Formula 2, according to the example embodiment, may provide characteristics required for the source compound, for example, a low melting point, a high vapor pressure, transportability in a liquid state, ease of vaporization, and a high thermal stability. Accordingly, it may be easy to perform a process of forming the lanthanum-containing film 448 by using the lanthanum compound having the structure of Chemical Formula 2, according to the example embodiment. Also, when the lanthanum compound having the structure of Chemical Formula 2, according to the example embodiment, is supplied into a hole having a relatively high aspect ratio to form the storage structure 440 of the non-volatile memory device 400A, the inside of the hole may have uniform step coverage characteristics with respect to a depth of the hole.

Figure 16:
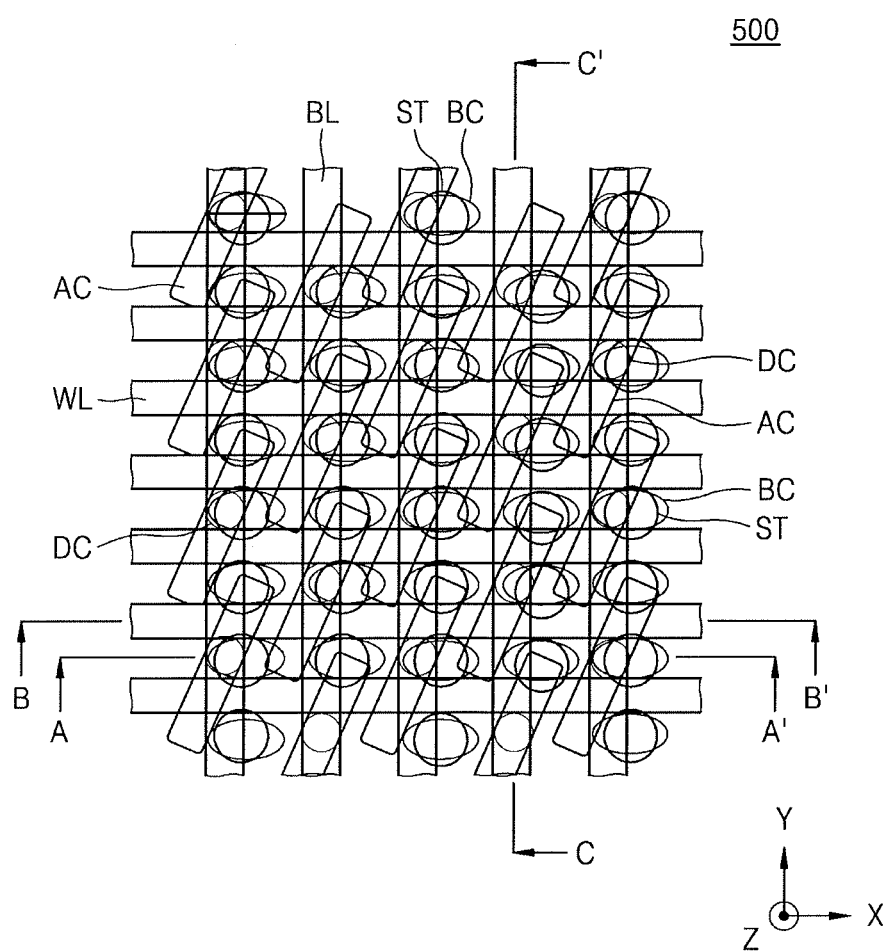
FIG. 16 illustrates a schematic plan layout of a cell array region of an IC device according to example embodiments.

FIG. 16 is a schematic plan layout of a cell array region of an IC device 500 according to example embodiments.

Referring to FIG. 16, the IC device 500 may include a plurality of active regions AC. A plurality of word lines WL may run across the plurality of active regions AC and extend parallel to one another in a first direction (refer to an X direction in FIG. 16). The plurality of word lines WL may be provided at regular intervals. A plurality of bit lines BL may be formed on the plurality of word lines WL and extend parallel to one another in a second direction (refer to a Y direction in FIG. 16) orthogonal to the first direction.

The plurality of bit lines BL may be connected to the plurality of active regions AC through a plurality of direct contacts DC.

Each of the plurality of buried contacts BC may include a contact structure, which may extend from a region between two adjacent ones of the plurality of bit lines BL to an upper portion of any one of the two adjacent bit lines BL. In some embodiments, the plurality of buried contacts BC may be arranged in rows in the first direction and the second direction. In some embodiments, the plurality of buried contacts BC may be arranged at regular intervals in the second direction. The plurality of buried contacts BC may serve to electrically connect lower electrodes ST of capacitors to the active regions AC.

The IC device 500 shown in FIG. 16 may include the lanthanum-containing film, which is obtained by using the lanthanum compound having the structure of Chemical Formula 2, according to the example embodiment.

Figure 17A:
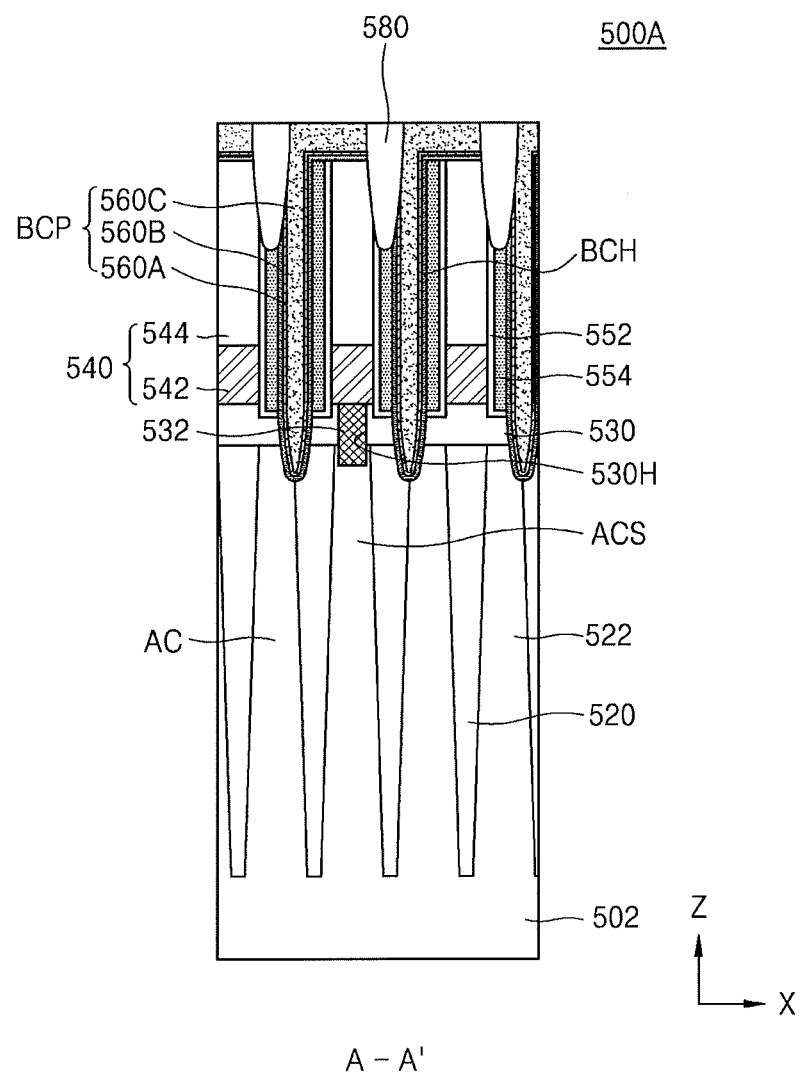
Figure 17B:
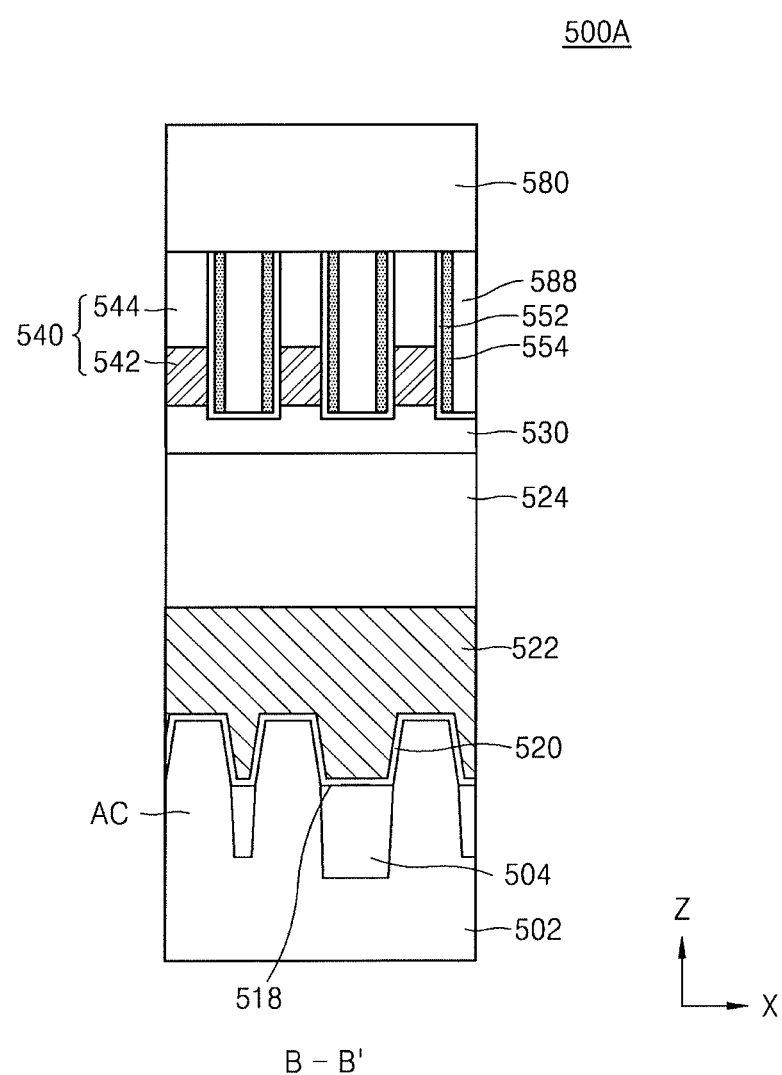
Figure 17C:
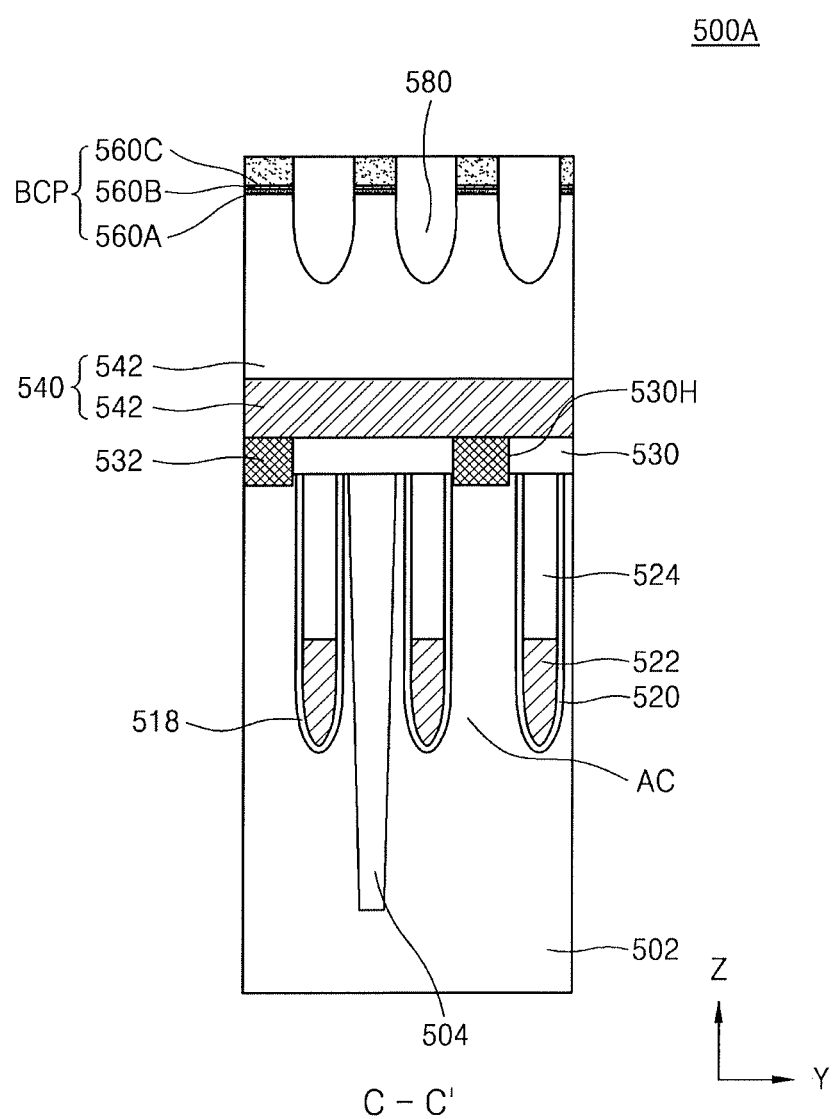

FIGS. 17A to 17C are diagrams of an IC device including a lanthanum-containing film, which is obtained by using the lanthanum compound having the structure of Chemical Formula 2, according to an example embodiment. FIGS. 17A to 17C are cross-sectional views of some elements of an example of a semiconductor memory device 500A, which may constitute a cell array region of the IC device 500 shown in FIG. 16. FIG. 17A is a cross-sectional view of some elements corresponding to the line A-A' of FIG. 16. FIG. 17B is a cross-sectional view of some elements corresponding to the line B-B' of FIG. 16. FIG. 17C is a cross-sectional view of some elements corresponding to the line C-C' of FIG. 16.

Referring to FIGS. 17A to 17C, a plurality of active regions AC may be defined by a device isolation layer 504 in a substrate 502 of a semiconductor memory device 500A.

Detailed descriptions of the substrate 502 are substantially the same as those of the substrate 302 presented with reference to FIGS. 12A to 12C.

A plurality of word line trenches 518 may be formed in the substrate 502. The plurality of word line trenches 518 may extend parallel to one another. Each of the plurality of word line trenches 518 may have a line shape across the plurality of active regions AC.

As shown in FIG. 17B, to form the plurality of word line trenches 518, each of which has a bottom surface with a step difference, the device isolation layer 504 and the substrate 502 may be etched by using separate etching processes such that an etch depth of the device isolation layer 504 is different form an etch depth of the substrate 502.

A gate dielectric film 520, a word line 522, and a buried insulating layer 524 may be sequentially formed in each of the plurality of word line trenches 518.

The gate dielectric film 520 may include a lanthanum-containing film, which is obtained by using a lanthanum compound having a structure of Chemical Formula 2, according to an example embodiment. For example, the gate dielectric film 520 may include a $La_2O_3$ film.

In some embodiments, the gate dielectric film 520 may be formed by using a lanthanum precursor composition formed of only the lanthanum compound CF-2 that is obtained by using the method described with reference to FIG. 1.

In some other embodiments, the gate dielectric film 520 may be formed by using a lanthanum precursor composition containing the lanthanum compound CF-2, which is obtained by using the method described with reference to FIG. 1, and a silicon-containing compound. The silicon-containing compound may include the silicon-containing intermediate CF-1, which is the reactant of Reaction Equation 3. The silicon-containing compound may be contained at a content of, for example, about 10 ppb to about 100 ppb, based on the total weight of the lanthanum precursor composition.

The word line 522 may include a conductive barrier film covering the gate dielectric film 520, and a conductive film formed on the conductive barrier film to fill a lower portion of the word line trench 518. In some embodiments, the conductive barrier film may be formed of, for example, Ti, TiN, Ta, TaN, or a combination thereof, and the conductive film may be formed of, for example, at least one material selected from the group of W, WN, TiSiN, and WSiN.

Source and drain regions may be formed on a top surface of each of the plurality of active regions AC.

A top surface of each of the plurality of word lines 522 may be located at a lower level than a top surface of the substrate 502. A bottom surface of each of the plurality of word lines 522 may have an uneven shape, and a saddle FinFET may be formed in each of the plurality of active regions AC.

The plurality of buried insulating layers 524 may include a silicon oxide film, a silicon nitride film, a silicon oxynitride film, or a combination thereof.

Insulating patterns 530 may be formed on the substrate 502. The insulating patterns 530 may include silicon oxide. The insulating patterns 530 may include a plurality of openings 530H, which may expose a plurality of source regions ACS of the plurality of active regions AC. A plurality of direct contacts 532 may be formed in the plurality of openings 530H and electrically connected to the source regions ACS of the active regions AC.

A plurality of bit line stack structures 540 may be formed on the insulating patterns 530 and the plurality of direct contacts 532 and extend parallel to one another. The plurality of bit line stack structures 540 may include a plurality of bit lines 542 and a plurality of insulating capping lines 544 covering top surfaces of the plurality of bit lines 542. The plurality of bit lines 542 may be electrically connected to the plurality of direct contacts 532.

In some embodiments, the plurality of bit lines 542 may include at least one material selected from the group of a doped semiconductor, a metal, a conductive metal nitride, or metal silicide. In some other embodiments, the plurality of bit lines 542 may have a multilayered structure including a first metal silicide film, a conductive barrier film, a second metal silicide film, and an electrode layer formed of a metal or a metal nitride, which are sequentially stacked. For example, the plurality of bit lines 542 may have a stack structure including a doped poly-Si layer, a TiN layer, and a tungsten layer that are sequentially stacked.

In some embodiments, the plurality of insulating capping lines 544 may include a silicon nitride film.

Both sidewalls of each of the plurality of bit line stack structures 540 may be covered with insulating spacers 552 and 554. The insulating spacers 552 and 554 may include a silicon oxide film, a silicon nitride film, or a combination thereof.

Although the present embodiment describes a case in which each of the insulating spacers 552 and 554 includes a double layer, each of the insulating spacers 552 and 554 may include, for example, a single layer or a triple layer.

As shown in FIG. 17A, a plurality of buried contact plugs BCP may be formed between the respective bit line stack structures 540 within a plurality of buried contact holes BCH. A width of each of the buried contact holes BCH in an X direction may be defined by the insulating spacers 552 and 554. The plurality of buried contact plugs BCP may include a lanthanum-containing film 560A, which is in contact with the active region AC of the substrate 502, a conductive barrier film 560B conformally covering the lanthanum-containing film 560A, and a contact plug 560C filling a space between the bit line stack structures 540 on the conductive barrier film 560B.

The lanthanum-containing film 560A may be obtained by using a lanthanum compound having a structure of Chemical Formula 2, according to an example embodiment. For example, the lanthanum-containing film 560A may include a $La_2O_3$ film. The lanthanum-containing film 560A may conformally cover sidewalls of the insulating spacers 552 and 554 and the surface of the active region AC.

In some embodiments, the lanthanum-containing film 560A may be formed by using a lanthanum precursor composition formed of only the lanthanum compound CF-2 that is obtained by using the method described with reference to FIG. 1.

In some other embodiments, the lanthanum-containing film 560A may be formed by using a lanthanum precursor composition including the lanthanum compound CF-2, which is obtained by using the method described with reference to FIG. 1, and a silicon-containing compound. The silicon-containing compound may include the silicon-containing intermediate CF-1, which is the reactant of Reaction Equation 3. The silicon-containing compound may be contained at a content of, for example, about 10 ppb to about 100 ppb, based on the total weight of the lanthanum precursor composition.

The conductive barrier film 560B may be formed of Ti. TiN, Ta, Ta, TaN, or a combination thereof, and the contact plug 560C may be formed of at least one material selected from the group of W, WN, TiSiN, and WSiN. However, materials forming the conductive barrier film 560B and the contact plug 560C are not limited to the examples.

FIG. 17C shows an example in which the plurality of buried contact plugs BCP extend from respective spaces between the plurality of bit line stack structures 540 to upper portions of the plurality of bit line stack structures 540, but, for example, the plurality of buried contact plugs BCP may be formed only in the respective spaces between the plurality of bit line stack structures 540.

Since the plurality of buried contact plugs BCP include the lanthanum-containing film 560A that is in direct contact with the active region AC, an ohmic contact may be formed between the plurality of buried contact plugs BCP and the active region AC through the lanthanum-containing film 560A. Thus, a resistance between the active region AC and the bit line structures 540 may be reduced, and a leakage current may be reduced. Also, in a process of manufacturing a highly scaled IC device having a ultrafine size, when spaces for forming the plurality of buried contact plugs BCP are very narrow and deep, the manufacturing process may be simplified because it is unnecessary to form a metal silicide film on the surface of the active region AC in bottom surfaces of the narrow and deep spaces. Also, the buried contact plugs BCP having a desired shape and profile may be formed even in the narrow and deep spaces.

As shown in FIG. 17B, insulating patterns 588 may be formed between the respective bit line stack structure 540 and between the respective buried contact plugs BCP.

The plurality of bit line stack structures 540 may be spaced apart from one another by insulating patterns 580. The insulating patterns 580 may include a silicon nitride film, but the inventive concept is not limited thereto.

Portions of the plurality of buried contact plugs BCP, which are provided on the plurality of bit line stack structures 540, may be used as landing pads configured to connect the plurality of buried contact plugs BCP with capacitors (not shown).

Figure 18A:
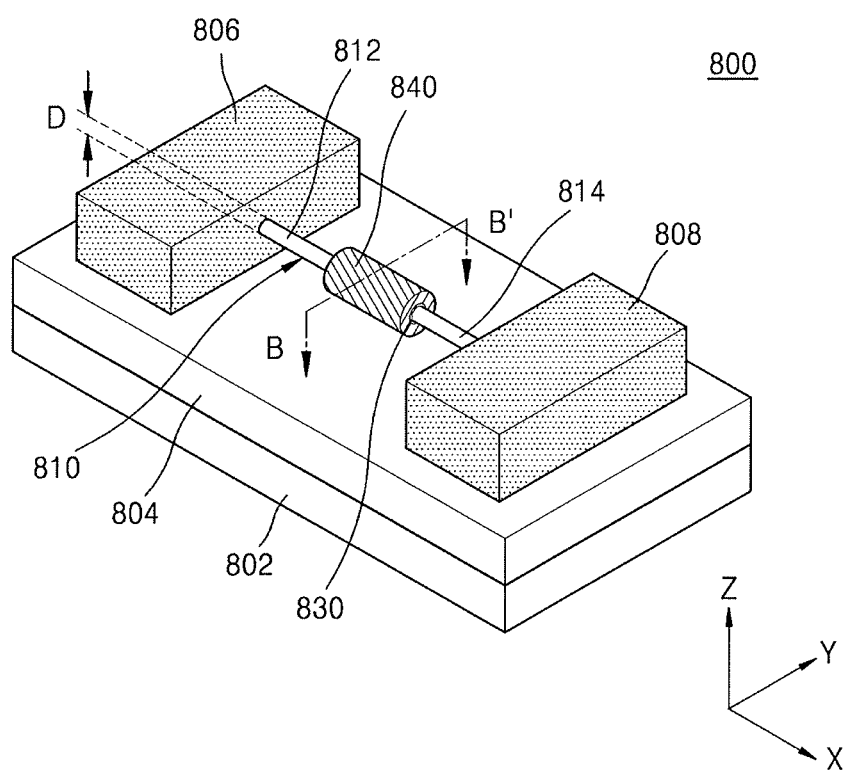
FIG. 18A illustrates a perspective view of an IC device according to example embodiments.
Figure 18B:
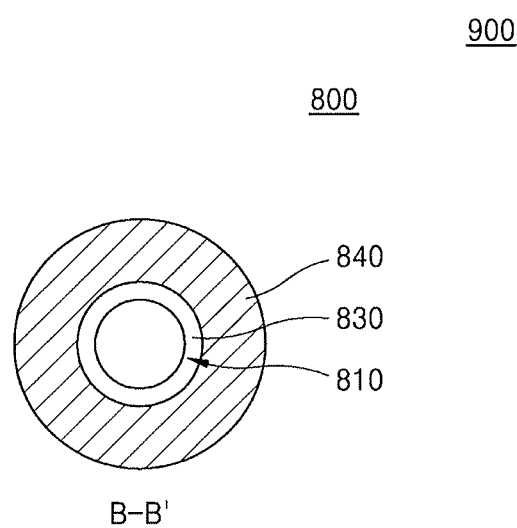
FIG. 18B illustrates a cross-sectional view taken along a line B-B' of FIG. 18A.

FIG. 18A is a perspective view of an IC device 800 according to example embodiments, and FIG. 18B is a cross-sectional view taken along a line B-B' of FIG. 18A.

Referring to FIGS. 18A and 18B, the IC device 800 may include a first pad region 806 and a second pad region 808 disposed on an insulating film 804 formed on a base substrate 802.

The base substrate 802 may include a semiconductor element (e.g., Si and Ge) or a compound semiconductor material (e.g., SiC, GaAs, InAs, and InP). The insulating film 804 may be formed of an oxide.

The first pad region 806 may be connected to the second pad region 808 by a semiconductor body 810 having a nanowire shape. The semiconductor body 810 may extend between the first pad region 806 and the second pad region 808 in a first direction (X direction) parallel to an extension direction of a main surface of the base substrate 802.

The first pad region 806 and the second pad region 808 may be unified with the semiconductor body 810. Materials forming the first pad region 806, the second pad region 808, and the semiconductor body 810 may be the same as described with reference to FIGS. 12A to 12C.

In some embodiments, the semiconductor body 810 may have a diameter D of about 30 nm or less. For example, the semiconductor body 810 may have a diameter of about 20 nm or less.

The IC device 800 may include a dielectric structure 830, which may surround the semiconductor body 810, and a gate electrode 840, which may cover the semiconductor body 810 such that the dielectric structure 830 is interposed between the gate electrode 840 and the semiconductor body 810.

The dielectric structure 830 may include a lanthanum-containing film, which is obtained by using the lanthanum compound having the structure of Chemical Formula 2, according to the example embodiment.

In some embodiments, the dielectric structure 830 may be formed by using a lanthanum precursor composition formed of only the lanthanum compound CF-2 that is obtained by using the method described with reference to FIG. 1.

In some other embodiments, the dielectric structure 830 may be formed by using a lanthanum precursor composition including the lanthanum compound CF-2, which is obtained by using the method described with reference to FIG. 1, and a silicon-containing compound. The silicon-containing compound may include the silicon-containing intermediate CF-1, which is the reactant of Reaction Equation 3. The silicon-containing compound may be contained at a content of, for example, about 10 ppb to about 100 ppb, based on the total weight of the lanthanum precursor composition.

The gate electrode 840 may include a metal or a conductive metal nitride. In some embodiments, the gate electrode 840 may have substantially the same stack structure as the gate electrode 320G described with reference to FIGS. 12A to 12C.

A doped source region 812 and a drain region 814 may be formed in the semiconductor body 810 on both sides of the gate electrode 840.

Figure 19:
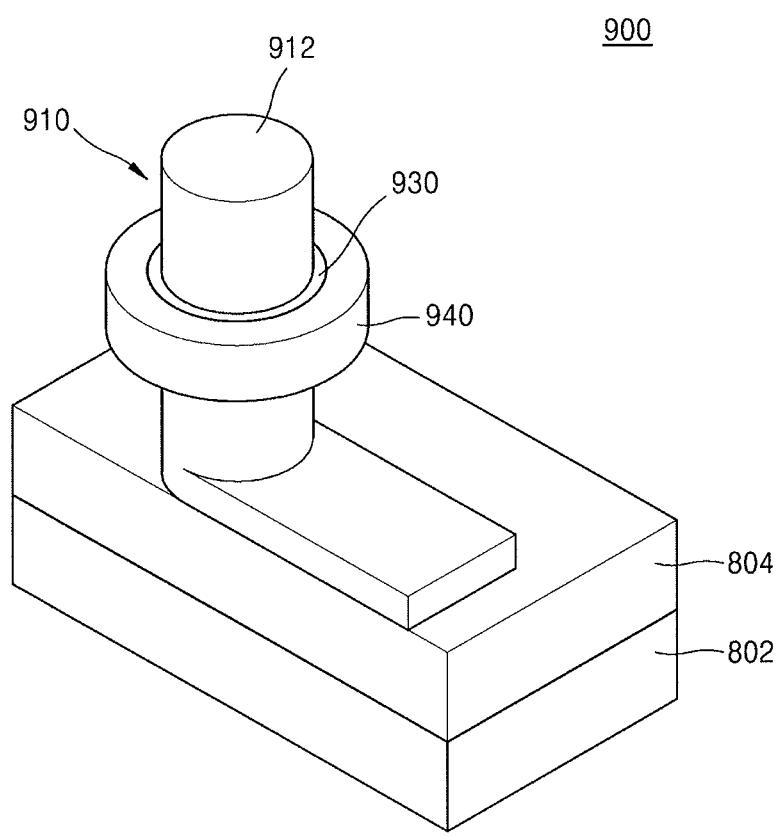
FIG. 19 illustrates a perspective view of an IC device according to example embodiments.

FIG. 19 is a perspective view of an IC device 900 according to example embodiments. In FIG. 19, the same reference numerals are used to denote the same elements as in FIGS. 18A and 18B, and detailed descriptions thereof are omitted.

Referring to FIG. 19, the IC device 900 may include a semiconductor layer 910 disposed on an insulating film 804 formed on a base substrate 802. The semiconductor layer 910 may include a semiconductor body 912, which may extend in a direction perpendicular to a main surface of the base substrate 802. The IC device 900 may include a dielectric structure 930 configured to surround the semiconductor body 912, and a gate electrode 940 covering the semiconductor body 912 such that the dielectric structure 930 is between the gate electrode 940 and the semiconductor body 912.

The dielectric structure 930 may include a lanthanum-containing film, which is obtained by using a lanthanum compound having a structure of Chemical Formula 2 according to an example embodiment.

In some embodiments, the dielectric structure 930 may be formed by using a lanthanum precursor composition formed of only the lanthanum compound CF-2 that is formed by using the method described with reference to FIG. 1.

In some other embodiments, the dielectric structure 930 may be formed by using a lanthanum precursor composition including the lanthanum compound CF-2, which is obtained by using the method described with reference to FIG. 1, and a silicon-containing compound. The silicon-containing compound may include the silicon-containing intermediate CF-1, which is the reactant of Reaction Equation 3. The silicon-containing compound may be contained at a content of, for example, about 10 ppb to about 100 ppb, based on the total weight of the lanthanum precursor composition.

The gate electrode 940 may include a metal or a conductive metal nitride. In some embodiments, the gate electrode 940 may be formed of the same material as the gate electrode 320G described with reference to FIGS. 12A to 12C.

In the semiconductor body 912, doped source and drain regions may be formed on both sides of the gate electrode 940.

Figure 20:
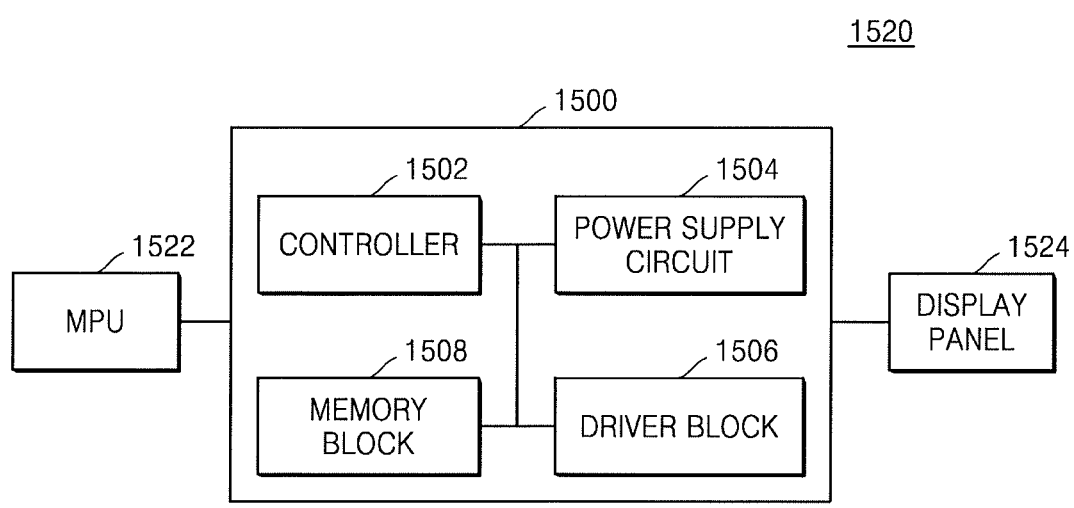
FIG. 20 illustrates a schematic block diagram of a display driver IC (DDI) and a display apparatus including the DDI according to example embodiments.

FIG. 20 is a schematic block diagram of a display driver IC (DDI) 1500 and a display apparatus 1520 including the DDI 1500 according to example embodiments.

Referring to FIG. 20, the DDI 1500 may include a controller 1502, a power supply circuit 1504, a driver block 1506, and a memory block 1508. The controller 1502 may receive a command applied from a main processing unit (MPU) 1522, decode the command, and control respective blocks of the DDI 1500 to embody an operation in response to the command. The power supply circuit 1504 may generate a driving voltage under the control of the controller 1502. The driver block 1506 may drive a display panel 1524 by using the driving voltage that is generated by the power supply circuit 1504 under the control of the controller 1502. The display panel 1524 may be a liquid crystal display (LCD) panel, a plasma display panel (PDP), or an organic light-emitting diode (OLED) display panel.

The memory block 1508 may be a block configured to temporarily store commands input to the controller 1502 or control signals output by the controller 1502 or store required data. The memory block 1508 may include a memory, such as RAM or ROM. At least one of the power supply circuit 1504 and the driver block 1506 may include at least one of the devices 300, 400, 400A, 500, 500A, 800, and 900 described with reference to FIGS. 12A to 19 and devices that are modified and changed within the scope of the inventive concept.

Figure 21:
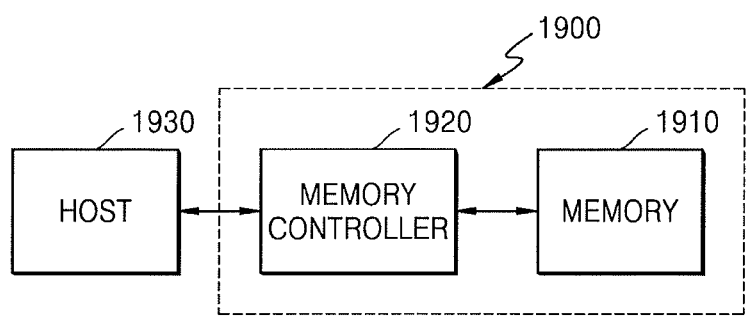
FIG. 21 illustrates a block diagram of an electronic system according to example embodiments.

FIG. 21 is a block diagram of an electronic system 1900 according to example embodiments.

The electronic system 1900 may include a memory 1910 and a memory controller 1920. The memory controller 1920 may control the memory 1910 to read data from the memory 1910 and/or write data to the memory 1910 in response to a request from a host 1930. At least one of the memory 1910 and the memory controller 1920 may include at least one of the devices 300, 400, 400A, 500, 500A, 800, and 900 described with reference to FIGS. 12A to 19 and devices that are modified and changed within the scope of the inventive concept.

Figure 22:
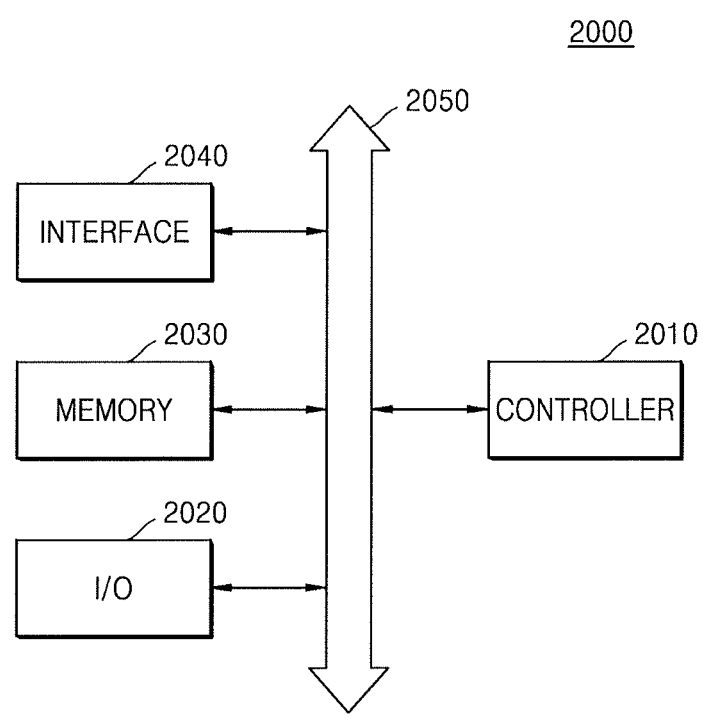
FIG. 22 illustrates a block diagram of an electronic system according to example embodiments.

FIG. 22 is a block diagram of an electronic system 2000 according to example embodiments.

The electronic system 2000 may include a controller 2010, an input/output (I/O) device 2020, a memory 2030, and an interface 2040, which may be connected to one another via a bus 2050.

The controller 2010 may include at least one of a microprocessor (MP), a digital signal processor (DSP), or similar processors thereto. The I/O device 2020 may include at least one of a keypad, a keyboard, or a display. The memory 2030 may be used to store commands executed by the controller 2010. For example, the memory 2030 may be used to store user data.

The electronic system 2000 may constitute a wireless communication device or a device capable of transmitting and/or receiving information in wireless environments. In the electronic system 2000, the interface 2040 may include a wireless interface to transmit/receive data via a wireless communication network. The interface 2040 may include an antenna and/or a wireless transceiver. In some embodiments, the electronic system 2000 may be used for a communication interface protocol of a third-generation communication system, for example, code division multiple access (CDMA), global system for mobile communications (GSM), north American digital cellular (NADC), extended-time division multiple access (E-TDMA), and/or wide band code division multiple access (WCDMA). The electronic system 2000 may include at least one of the devices 300, 400, 400A, 500, 500A, 800, and 900 described with reference to FIGS. 12A to 19 and devices that are modified and changed within the scope of the inventive concept.

By way of summation and review, forming lanthanum-containing thin films having good gap-fill characteristics and good step coverage characteristics in narrow, deep spaces having a high aspect ratio may help advance the production of highly integrated IC devices having high operating speed and high reliability.

As described above, embodiments relate to a lanthanum compound, which is a liquid at room temperature, a method of synthesizing the lanthanum compound, a lanthanum precursor composition containing the lanthanum compound, a method of forming a thin film using the lanthanum precursor composition, and a method of manufacturing an IC device using the lanthanum precursor composition.

Embodiments may provide a lanthanum compound having appropriate characteristics for a source compound for forming a lanthanum-containing film. Embodiments may also provide a method of synthesizing a lanthanum compound, by which a lanthanum compound having appropriate characteristics for a source compound for forming a lanthanum-containing film may be easily synthesized. Embodiments may also provide a method of forming a thin film by using a lanthanum compound having appropriate characteristics for a precursor for forming a lanthanum-containing film. Embodiments may also provide a method of manufacturing an integrated circuit (IC) device, which includes a process of forming a lanthanum-containing film having good step coverage characteristics.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound of the following Chemical Formula 1:

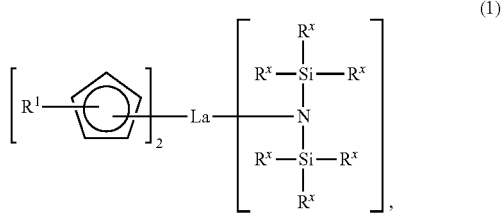

wherein $R^1$ is a C1-C4 linear or branched alkyl group, and each $R^x$ is independently a C1-C2 alkyl group.

2. The compound as claimed in claim 1, wherein the compound is pure.

3. A method of forming the compound as claimed in claim 1, the method comprising:
reacting a lanthanum tris(alkylsilylamide) complex with an alkylcyclopentadiene, wherein:
in the lanthanum tris(alkylsilylamide) complex, the alkyl groups are each independently a C1-C2 alkyl group, and
in the alkylcyclopentadiene, the alkyl group is a C1-C4 linear or branched alkyl group.

4. The method as claimed in claim 3, further comprising purifying the resultant of the reaction of the lanthanum tris(alkylsilylamide) complex with the alkylcyclopentadiene.

5. The method as claimed in claim 4, wherein the purifying includes sublimation of the compound represented by Chemical Formula 1.

6. A method of manufacturing an integrated circuit (IC) device using the compound as claimed in claim 1, the method comprising:
forming a lower structure on a substrate; and
forming a lanthanum-containing film on the lower structure, the lanthanum-containing film being produced by deposition of lanthanum-containing species from a composition that includes the compound represented by Chemical Formula 1 and a compound represented by the following Chemical Formula 2:

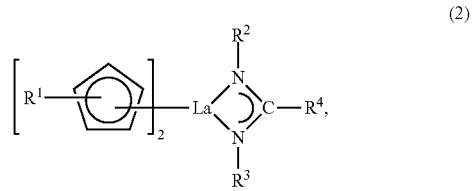

wherein, in Chemical Formula 2, $R^1$ is a C1-C4 linear or branched alkyl group, each of $R^2$ and $R^3$ is independently a C1-C4 linear or branched alkyl group, and $R^4$ is hydrogen or a methyl group.

7. A synthesis method, the method comprising:

synthesizing a silicon-containing intermediate of Chemical Formula 1 by reacting a lanthanum tris[bis(trialkylsilyl)amide] complex with an alkylcyclopentadiene,

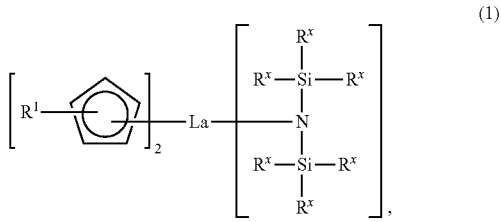 (1)

wherein $R^1$ is a C1-C4 linear or branched alkyl group, and each $R^x$ is independently a C1-C2 alkyl group; and synthesizing a lanthanum compound of Chemical Formula 2 by reacting the silicon-containing intermediate of Chemical Formula 1 with a dialkylamidine-based compound,

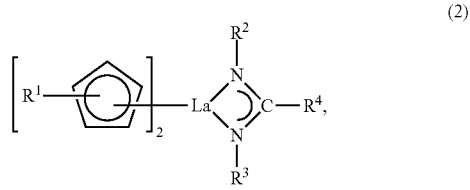 (2)

wherein $R^1$ is a C1-C4 linear or branched alkyl group, each of $R^2$ and $R^3$ is independently a C1-C4 linear or branched alkyl group, and $R^4$ is hydrogen atom or a methyl group.

8. The method as claimed in claim 7, wherein in the silicon-containing intermediate of Chemical Formula 1, $R^x$ is a methyl group.

9. The method as claimed in claim 7, wherein the lanthanum compound of Chemical Formula 2 is a liquid at room temperature.

10. The method as claimed in claim 7, wherein the dialkylamidine-based compound is formed from diisopropyl acetamidine.

11. The method as claimed in claim 7, wherein in the lanthanum compound of Chemical Formula 2, $R^1$ is an ethyl group, each of $R^2$ and $R^3$ is an isopropyl group, and $R^4$ is a methyl group.

12. The method as claimed in claim 7, wherein in the lanthanum compound of Chemical Formula 2, each of $R^1$, $R^2$, and $R^3$ is an isopropyl group, and $R^4$ is a methyl group.

13. The method as claimed in claim 7, wherein in the lanthanum compound of Chemical Formula 2, $R^1$ is an isopropyl group, each of $R^2$ and $R^3$ is a t-butyl group, and $R^4$ is a methyl group.

14. The method as claimed in claim 7, further comprising, before the synthesizing of the silicon-containing intermediate, synthesizing the lanthanum tris[bis(trialkylsilyl)amide] complex by reacting a lanthanum halide with a bis(trialkylsilyl)amide alkali metal salt.

15. The method as claimed in claim 14, wherein the lanthanum halide is $LaCl_3$.

16. The method as claimed in claim 14, wherein the bis(trialkylsilyl)amide alkali metal salt includes sodium (Na), lithium (Li), or potassium (K).

* * * * *